US012685647B2

(12) United States Patent　　　　(10) Patent No.:　US 12,685,647 B2
Ahn　　　　　　　　　　　　　　　　(45) Date of Patent:　　　Jul. 21, 2026

---

(54) BOX-SHAPED SPINAL CAGE STRUCTURE

(71) Applicants:GBS Commonwealth Co., Ltd., Seoul (KR); PMT Republic, Inc., Walnut, CA (US)

(72) Inventor:　Kyoung Gee Ahn, Seoul (KR)

(73) Assignees: GBS Commonwealth Co., Ltd., Seoul (KR); PMT Republic, Inc., Walnut, CA (US)

( * ) Notice:　Subject to any disclaimer, the term of this patent is extended or adjusted under 35 U.S.C. 154(b) by 0 days.

(21) Appl. No.: 18/824,943

(22) Filed:　Sep. 5, 2024

(65)　　　　　Prior Publication Data

US 2026/0053638 A1　　Feb. 26, 2026

(30)　　　Foreign Application Priority Data

Aug. 21, 2024　(KR) ........................ 10-2024-0112253

(51) Int. Cl.
　　*A61F 2/44*　　　　(2006.01)
　　*A61F 2/28*　　　　(2006.01)
　　*A61F 2/30*　　　　(2006.01)
(52) U.S. Cl.
　　CPC ...... *A61F 2/447* (2013.01); *A61F 2002/2835* (2013.01); *A61F 2002/30593* (2013.01)
(58) Field of Classification Search
　　CPC .............. A61F 2/447; A61F 2002/2835; A61F 2002/30593; A61F 2/442; A61F 2/443; A61F 2/4445; A61F 2/4455; A61F 2/446; A61F 2/4465
　　See application file for complete search history.

(56)　　　　　　References Cited

U.S. PATENT DOCUMENTS

| | | | |
|---|---|---|---|
| 9,883,953 B1 * | 2/2018 | To ......................... | A61F 2/4455 |
| 12,064,355 B1 | 8/2024 | Robbins | |
| 2008/0161925 A1 * | 7/2008 | Brittan ................... | A61F 2/4611 |
| | | | 623/17.16 |
| 2008/0172128 A1 * | 7/2008 | Perez-Cruet .......... | A61F 2/4455 |
| | | | 623/17.15 |
| 2008/0262623 A1 | 10/2008 | Bagga et al. | |
| 2009/0043342 A1 * | 2/2009 | Freedland ............. | A61F 2/3662 |
| | | | 606/301 |

(Continued)

FOREIGN PATENT DOCUMENTS

| | | |
|---|---|---|
| CN | 210354995 U | 4/2020 |
| CN | 112315629 A | 2/2021 |

(Continued)

*Primary Examiner* — Eduardo C Robert
*Assistant Examiner* — Holly Joanna Lane
(74) *Attorney, Agent, or Firm* — NKL Law; Jae Youn Kim

(57)　　　　　　　ABSTRACT

Disclosed is a box-shaped spinal cage structure including a cage body configured to have an internal space formed therein, an upper blocking part coupled to an upper surface of the cage body to block the internal space of the cage body from outside, a lower blocking part coupled to a lower surface of the cage body to block the internal space of the cage body from the outside, and a rear insertion hole formed through a rear surface of the cage body so that a bone graft is inserted into the internal space of the cage body through the rear insertion hole, so wherein the upper and lower surfaces of the cage body are blocked from the outside to prevent loss of the bone graft in the cage body.

11 Claims, 38 Drawing Sheets

(56) References Cited

U.S. PATENT DOCUMENTS

| 2010/0152784 | A1* | 6/2010 | Lowry | A61B 17/8028 |
| | | | | 623/17.11 |
| 2022/0241088 | A1* | 8/2022 | Giri | A61F 2/4455 |
| 2024/0016622 | A1* | 1/2024 | Jimenez | A61F 2/4455 |

FOREIGN PATENT DOCUMENTS

| CN | 219126893 U | 6/2023 | |
| KR | 101502061 B1 | 3/2015 | |
| KR | 20200101115 A | 8/2020 | |
| KR | 20240019466 A | 2/2024 | |
| WO | WO-2021055363 A1 * | 3/2021 | A61F 2/4611 |

* cited by examiner

BOX-SHAPED SPINAL CAGE STRUCTURE

CROSS REFERENCE TO RELATED APPLICATIONS

This U.S. non-provisional application claims priority under 35 U.S.C. 119 of Korean Patent Application No. 10-2024-0112253, filed on Aug. 21, 2024, the entire contents of which are hereby incorporated by reference.

BACKGROUND OF THE INVENTION

Field of the Invention

The present invention relates to a spinal cage structure, and more particularly, to a box-shaped spinal cage structure.

Description of the Related Art

The spine may have structural problems, such as a problem in stable alignment or narrowing of a distance between vertebral bodies, for congenital or degenerative reasons, or other reasons, such as accidents.

Representative spinal diseases include spinal deformities, spinal fractures, spinal disc herniation, spinal stenosis, posterior joint hypertrophy, etc., and these spinal diseases require surgical treatment when symptoms worsen and conservative treatment becomes difficult.

Among surgical treatment methods, spinal fusion is a procedure in which an intervertebral disc in which a spinal disease occurred is removed and then a spinal cage is inserted between vertebral bodies to secure a space into which the bone grows and enters for fusion, increase a distance between the vertebral bodies to reduce pain, and restore lordosis of the spine to maintain stability of the spine.

Generally, a spinal cage used in spinal fusion surgery has a space formed therein so that a bone graft is inserted into the space, and as the bone graft is regenerated, bone fusion is achieved between upper and lower vertebrae.

Various types of spinal cages have been developed depending on the surgical method or the like, and shapes of spinal cages to restore biomechanical stability of the spine while being implantable into the human body are being developed in various ways.

However, the conventional spinal cage has a problem in that, when the spinal cage is inserted into the human body in the state in which a cage body is filled with a bone graft, an impact occurs, and at this time, a large amount of the bone graft falls out of the cage body and is lost.

In addition, after the conventional spinal cage is inserted into the human body, the lost amount of the bone graft must be additionally supplemented, but there is a problem in that a process of supplementing the bone graft into the spinal cage that has already been inserted into the human body is not easy.

The matters described above as background technology are only for enhancement of understanding of the background of the invention, and should not be taken as recognition that they correspond to prior art already known to those skilled in the art.

SUMMARY OF THE INVENTION

Therefore, the present invention has been made in view of the above problems, and it is an object of the present invention to provide a box-shaped spinal cage structure in which the upper and lower surfaces of a cage body are shut off from the outside to prevent loss of a bone graft in the cage body.

It is another object of the present invention to provide a box-shaped spinal cage structure in which the upper, lower, and both side surfaces of a cage body are formed with porosity to enable stable bone fusion.

The objects of the present invention are not limited to the above-mentioned objects, and other objects not mentioned herein will be clearly understood by those skilled in the art from the following description.

In accordance with the present invention, the above and other objects can be accomplished by the provision of a box-shaped spinal cage structure including a cage body configured to have an internal space formed therein, an upper blocking part coupled to an upper surface of the cage body to block the internal space of the cage body from outside, a lower blocking part coupled to a lower surface of the cage body to block the internal space of the cage body from the outside, and a rear insertion hole formed through a rear surface of the cage body so that a bone graft is inserted into the internal space of the cage body through the rear insertion hole, wherein a plurality of upper pores is perforated in the upper blocking part and a plurality of lower pores is perforated in the lower blocking part so that the upper blocking part and the lower blocking part are formed with porosity.

A plurality of left and right structures having a hollow interior may be stacked on both side surfaces of the cage body.

A plurality of left and right structures having a hollow interior may be stacked on one side surface of the cage body, a side window having a larger size than a size of the hollow interiors of the left and right structures may be formed in the side surface of the cage body by cutting so that the bone graft is inserted into the internal space of the cage body through the side window, and a plurality of left and right structures having a hollow interior may be stacked on a remaining side surface of the cage body.

The box-shaped spinal cage structure may further include at least one upper window formed by cutting one side of the upper blocking part and having a larger size than a diameter of the plurality of upper pores, and at least one lower window formed by cutting one side of the upper blocking part and having a larger size than a diameter of the plurality of lower pores, and the bone graft may be inserted into the internal space of the cage body through the at least one upper window and the at least one lower window.

The box-shaped spinal cage structure may further include at least one upper window formed by cutting one side of the upper blocking part and having a larger size than a diameter of the plurality of upper pores, the bone graft may be inserted into the internal space of the cage body through the at least one upper window, and only the plurality of lower pores may be formed in the lower blocking part.

The box-shaped spinal cage structure may further include a front fastening part formed on a front surface of the cage body, a front fastening pin coupled to the front fastening part in upward and downward directions, and a front rotating part rotatably mounted on the front surface of the cage body via the front fastening pin, the front rotating part may be mounted to open and close the front surface of the cage body, and when the front rotating part is opened, the bone graft may be inserted into the internal space of the cage body through the front surface of the cage body.

The box-shaped spinal cage structure may further include a pair of front rails coupled to a front surface of the cage body in leftward and rightward directions, and a front sliding part having a pair of sliding grooves formed in a rear surface thereof so that the pair of front rails is slidably fastened to the pair of sliding grooves, the front sliding part may be mounted to open and close the front surface of the cage body, and when the front sliding part is opened, the bone graft may be inserted into the internal space of the cage body through the front surface of the cage body.

The box-shaped spinal cage structure may further include a front protrusion formed to protrude from the front surface of the cage body, and a sliding engagement part formed to be recessed in one side of the front sliding part and disposed to face the front protrusion to be engaged with the front protrusion.

The box-shaped spinal cage structure may further include a pair of front engagement parts formed to protrude inwardly from both inner sides of a front surface of the cage body, and a front locking part having a pair of hooks formed to protrude rearwardly from a rear surface of the front locking part to be hooked and fastened to the pair of front engagement parts, the hooks may be formed of a material having elastic restoring force to be deformable in leftward and rightward directions, the front locking part may be mounted to open and close the front surface of the cage body, and when the front locking part is opened, the bone graft may be inserted into the internal space of the cage body through the front surface of the cage body.

The box-shaped spinal cage structure may further include engagement slopes formed on front surfaces of the front engagement parts as inclined surfaces having a predetermined angle, and hook slopes formed on rear surfaces of the hooks as inclined surfaces having a predetermined angle.

The box-shaped spinal cage structure may further include a set screw inserted and fastened into the rear insertion hole to block the internal space of the cage body from the outside.

A screw hole may be formed through a center of the set screw, and a diameter of the screw hole may be smaller than a diameter of the rear insertion hole.

The box-shaped spinal cage structure may further include a rear fastening pin coupled to the rear surface of the cage body in upward and downward directions, and a rear rotating part mounted rotatably on the rear surface of the cage body via the rear fastening pin, the rear rotating part may be mounted to open and close the rear insertion hole, and when the rear rotating part is closed, the bone graft may not be discharged outside the cage body through the rear insertion hole.

The box-shaped spinal cage structure may further include a rear lateral hole perforated in leftward and rightward directions in the rear surface of the cage body, and a rear movable part disposed in the rear lateral hole to move left and right within the rear lateral hole, the rear movable part may be mounted to open and close the rear insertion hole, and when the rear movable part is closed, the bone graft may not be discharged outside the cage body through the rear insertion hole.

The box-shaped spinal cage structure may further include a device fixing unit inserted into the rear insertion hole and configured to accommodate the bone graft therein, and an impactor configured to enter an inside of the device fixing unit to insert the bone graft accommodated in the device fixing unit into the internal space of the cage body.

BRIEF DESCRIPTION OF THE DRAWINGS

The above and other objects, features and other advantages of the present invention will be more clearly under-

Figure 1:
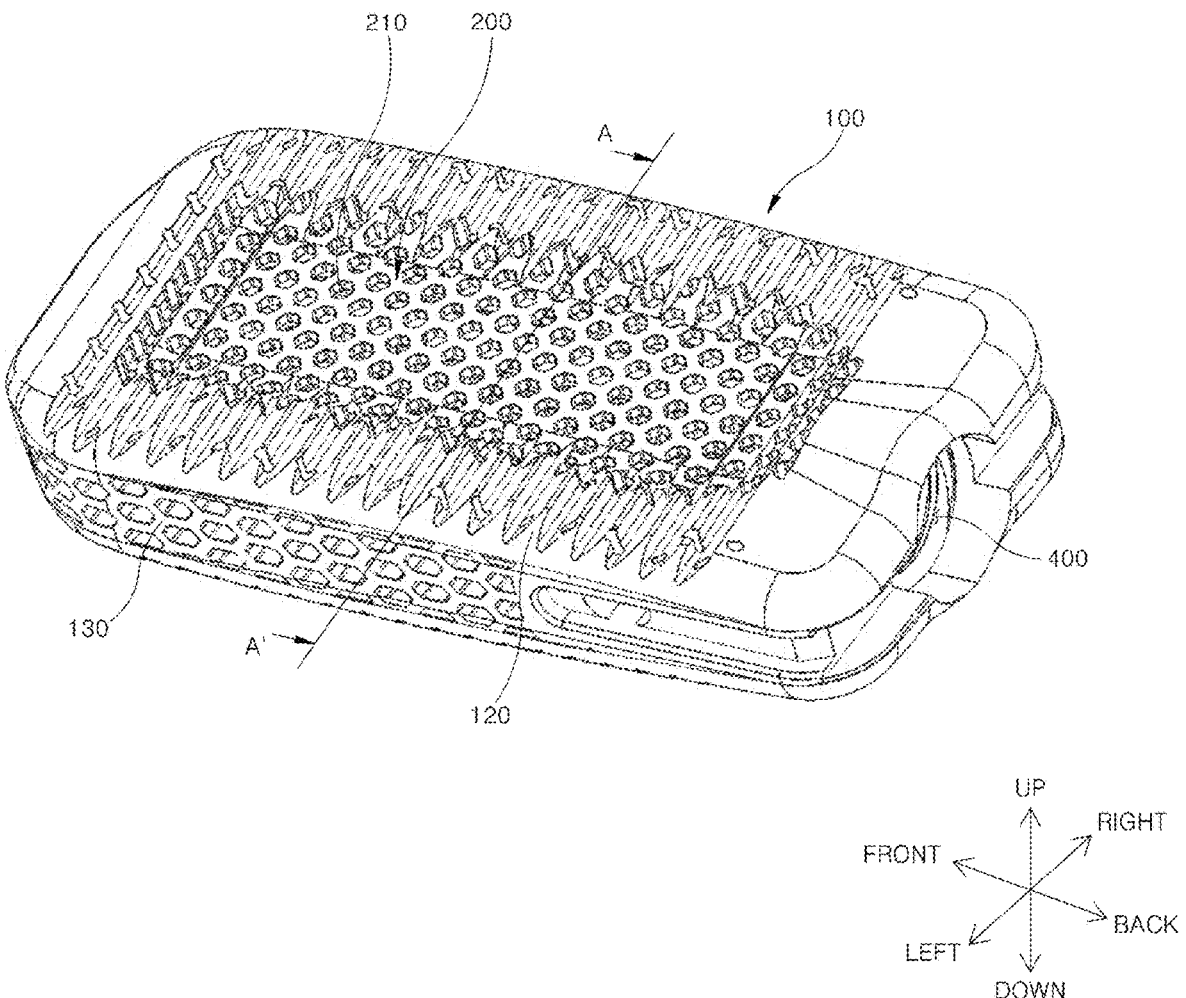
Figure 2:
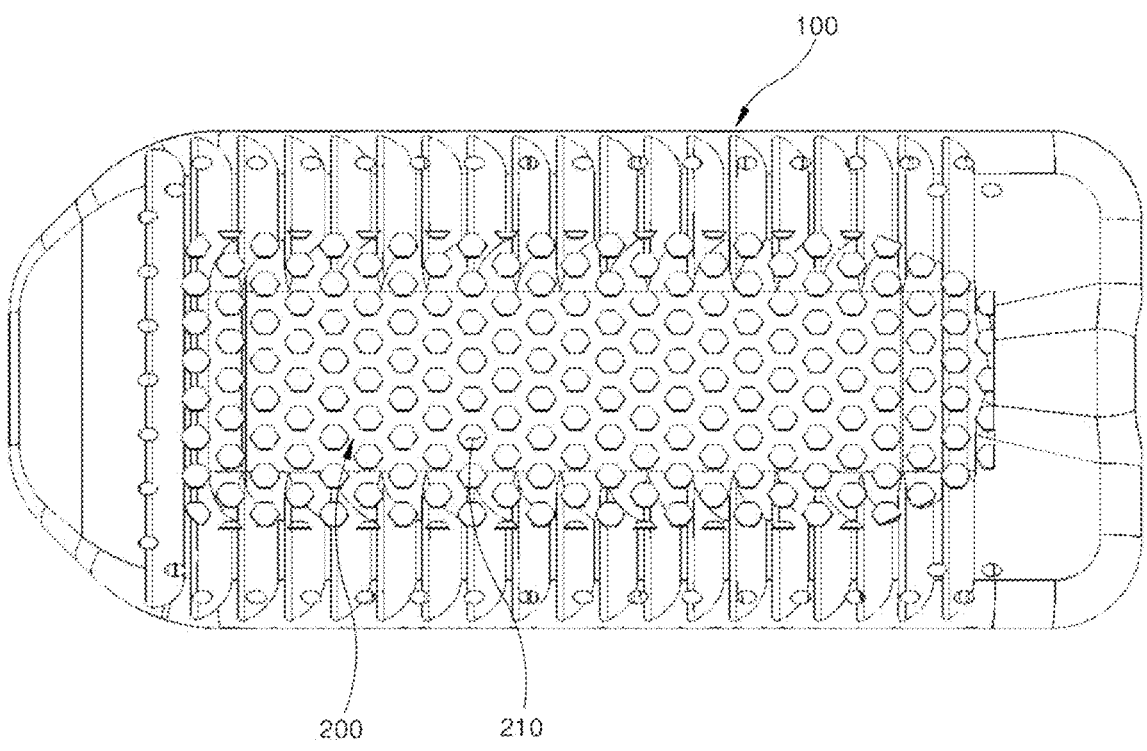
Figure 3:
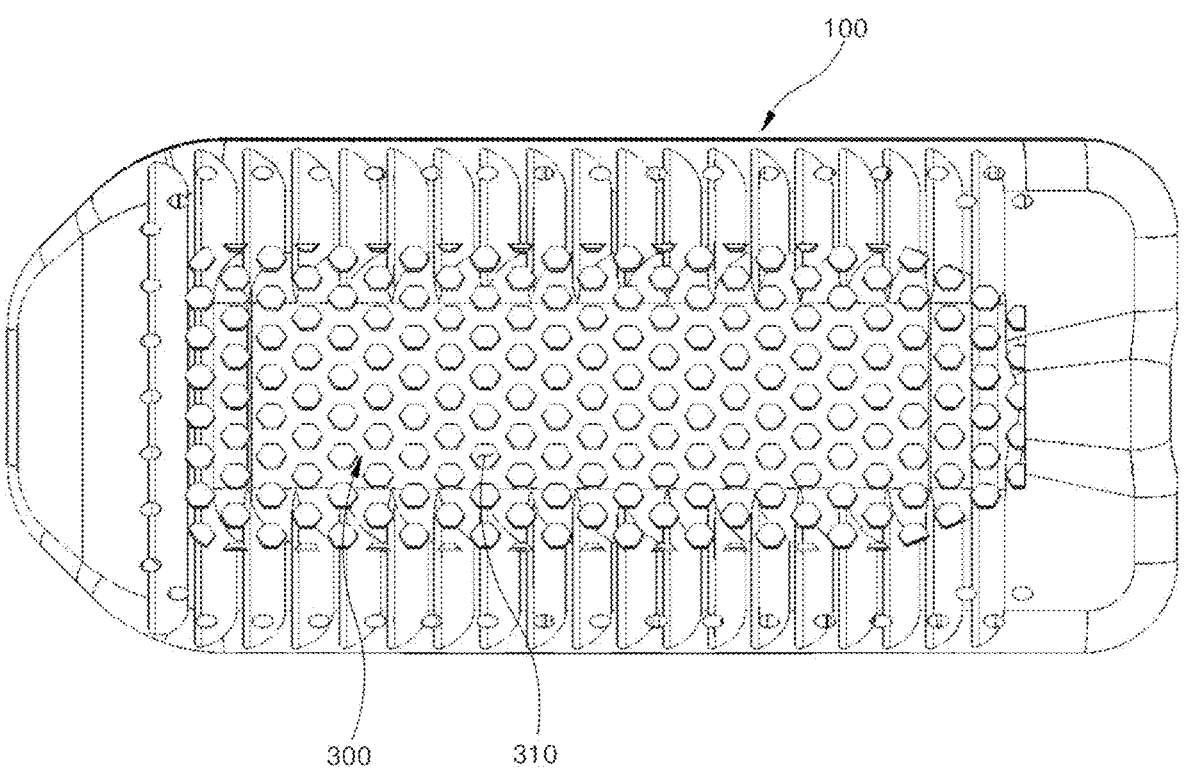
Figure 4:
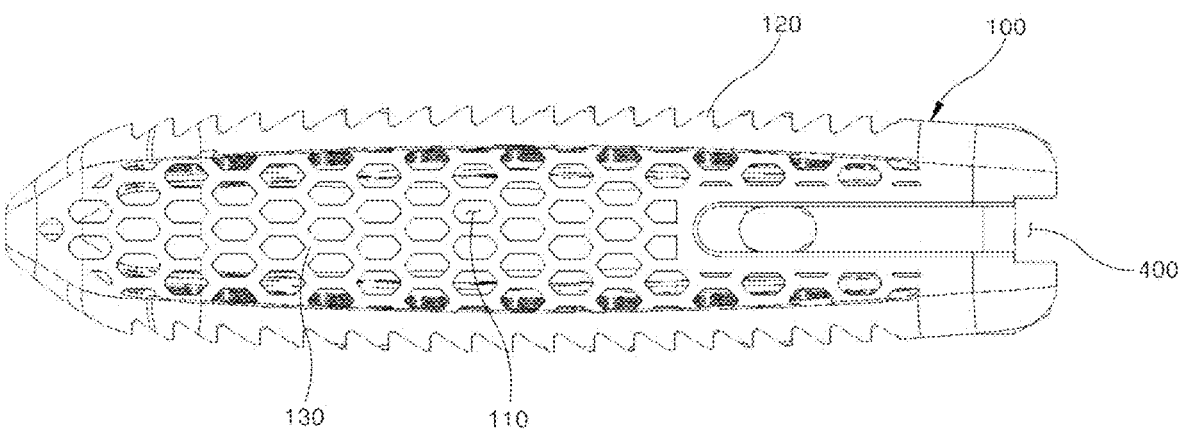
Figure 5:
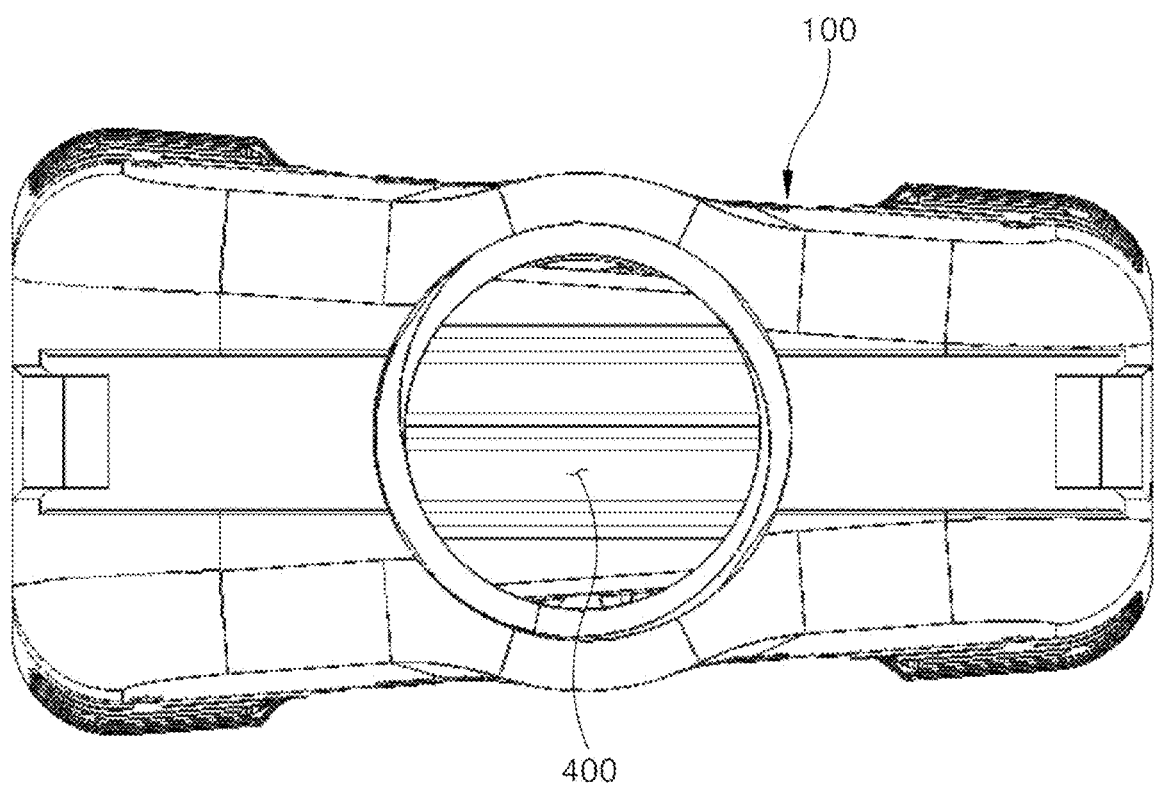
Figure 6:
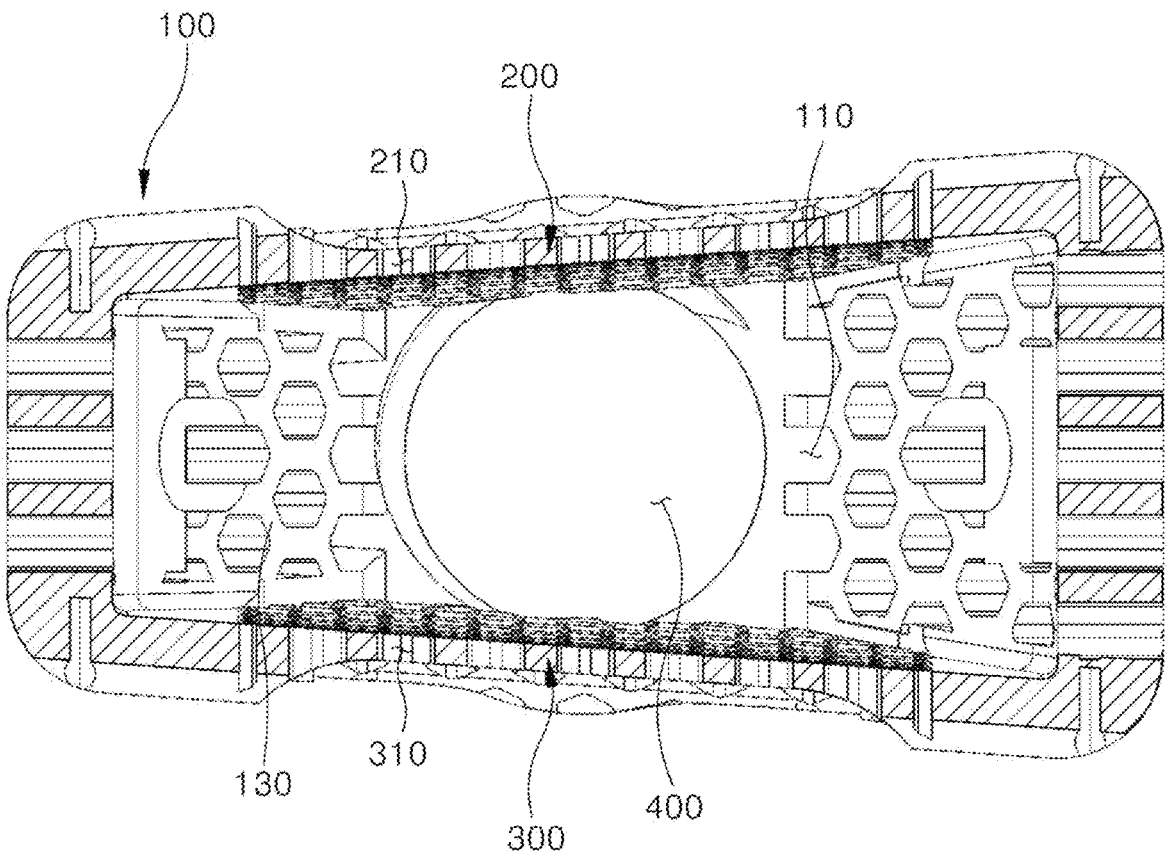
Figure 7:
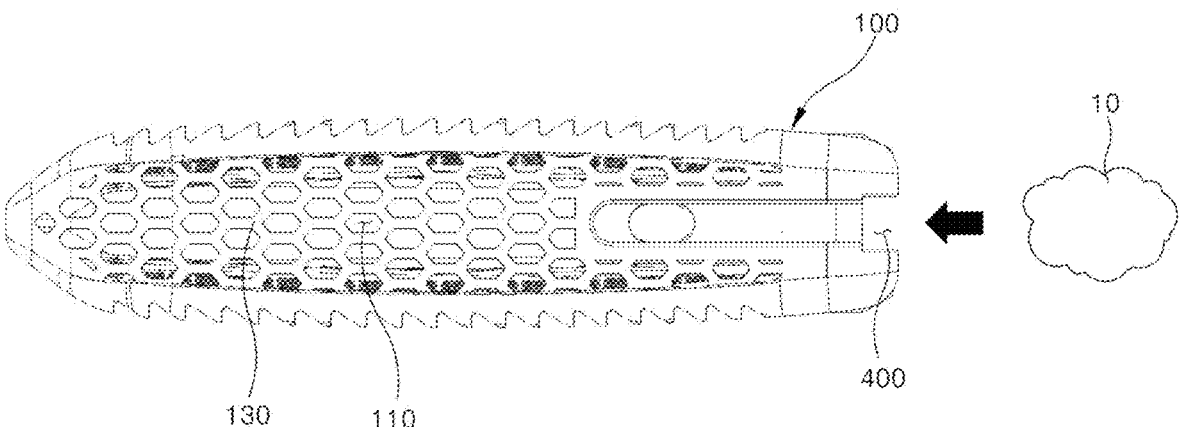
Figure 8:
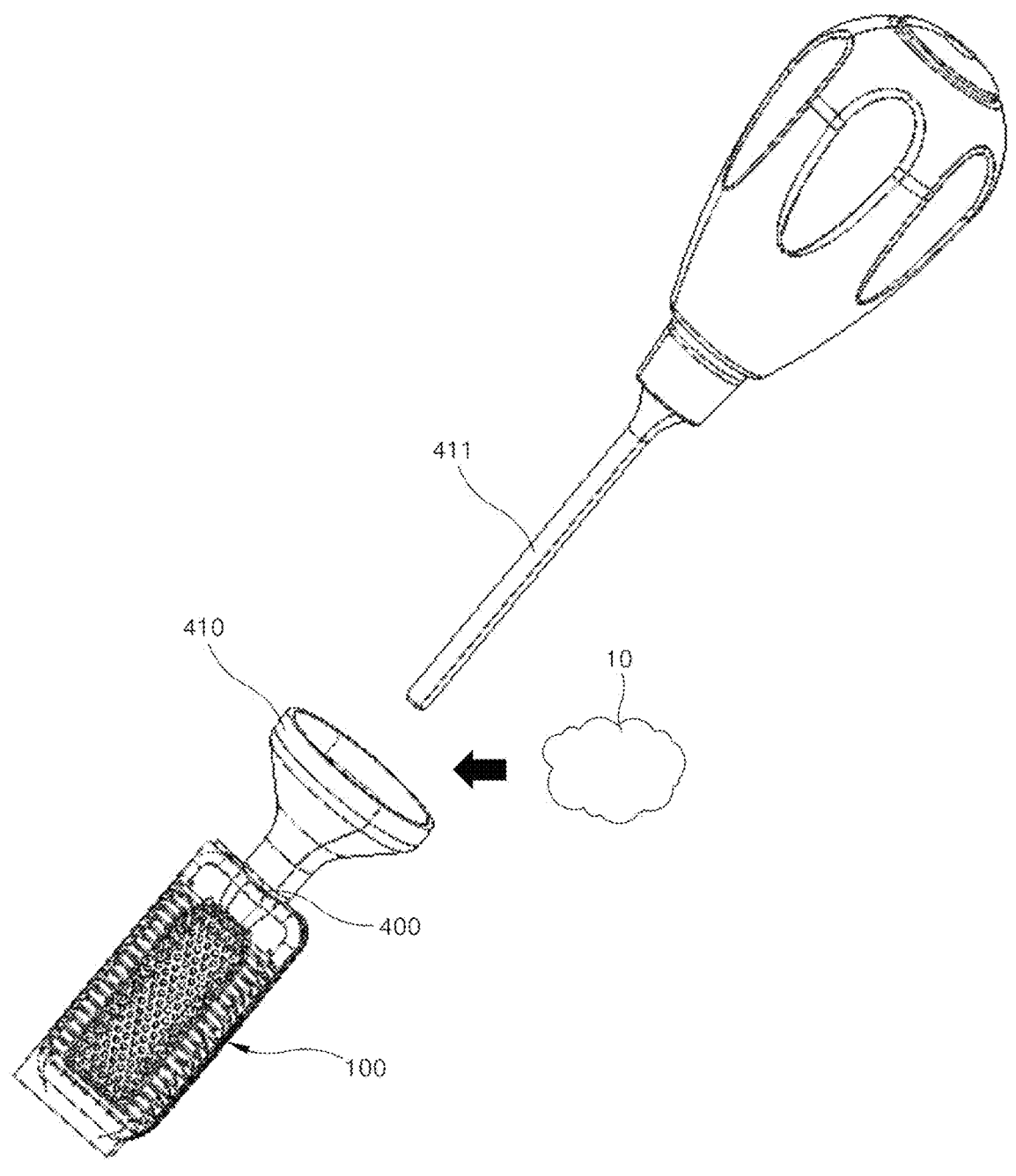
Figure 9:
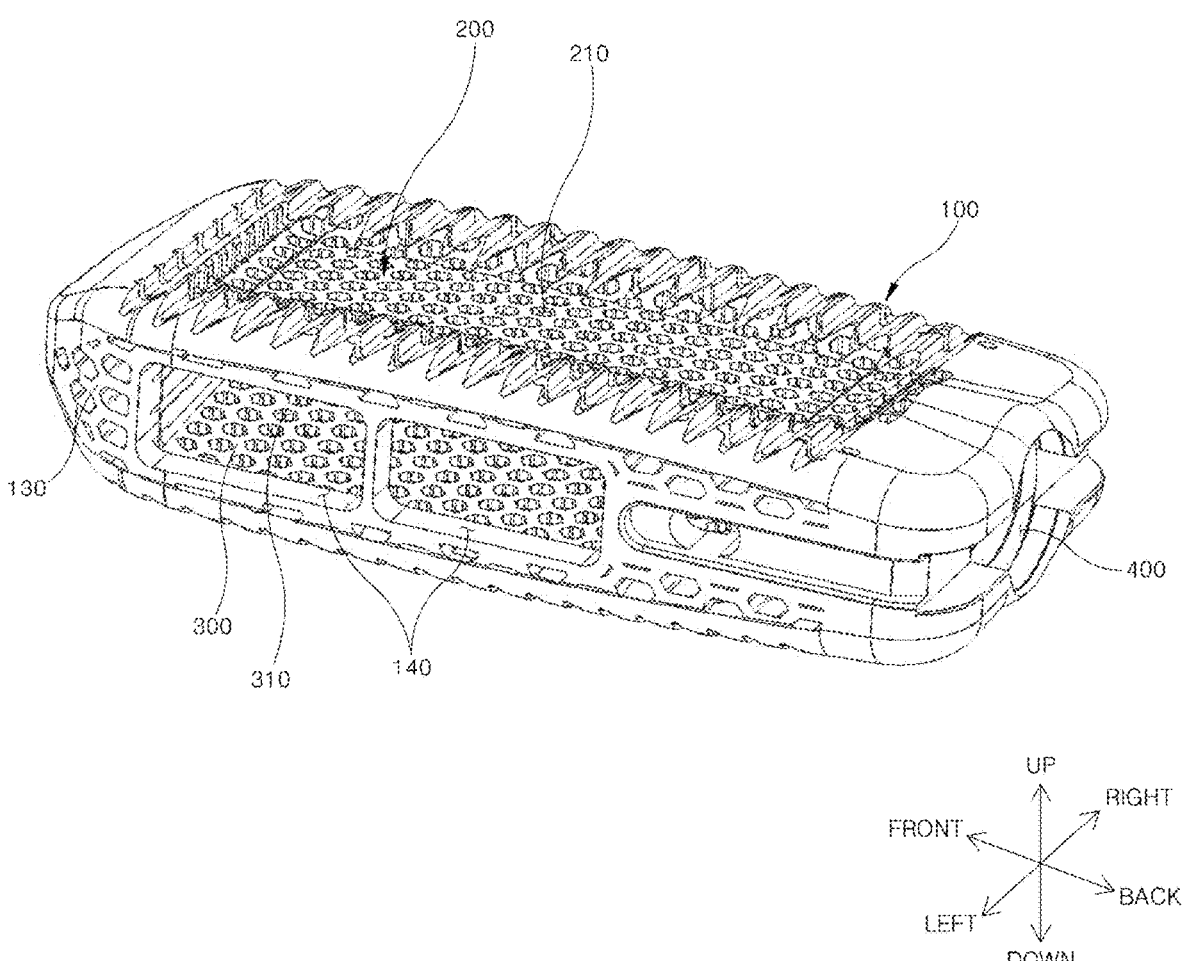
Figure 10:
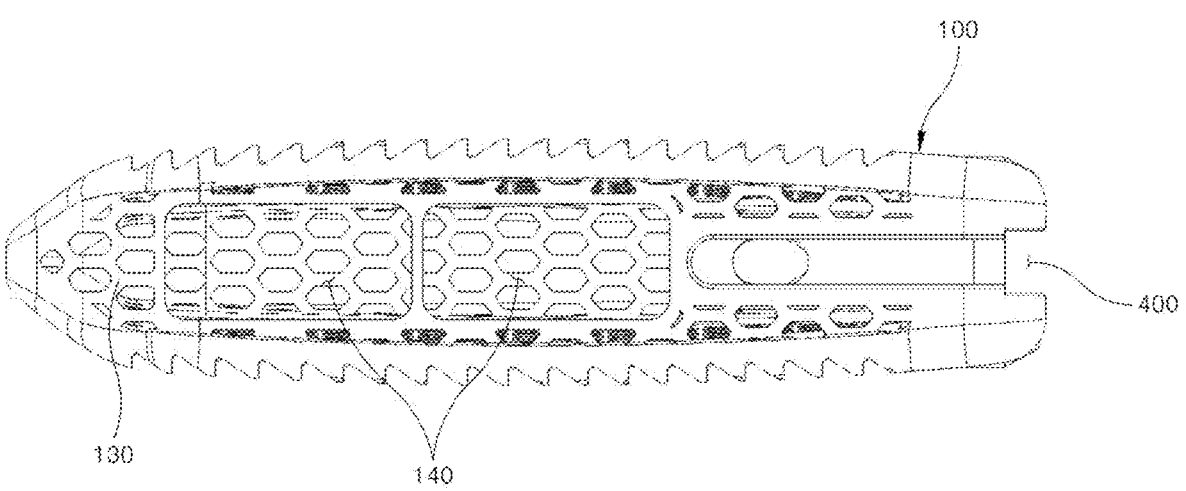
Figure 11:
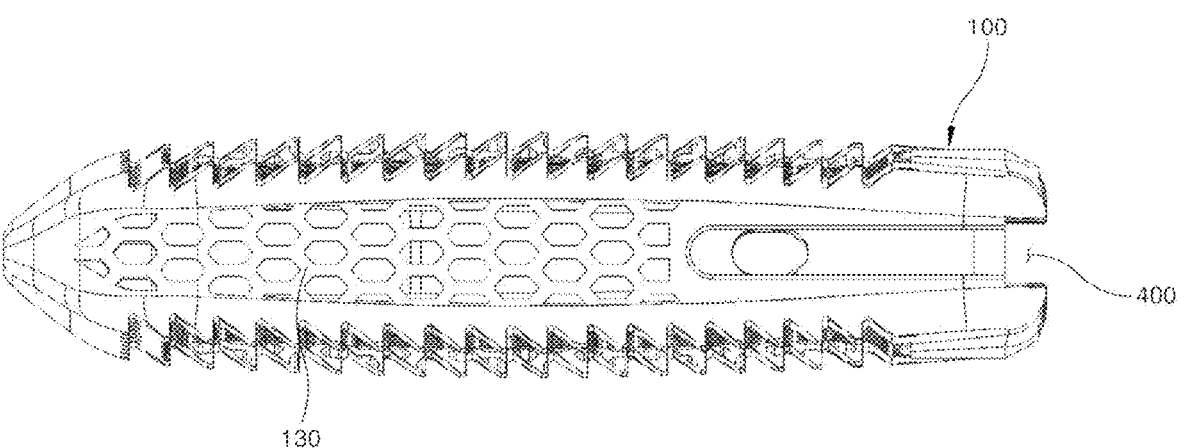
Figure 12:
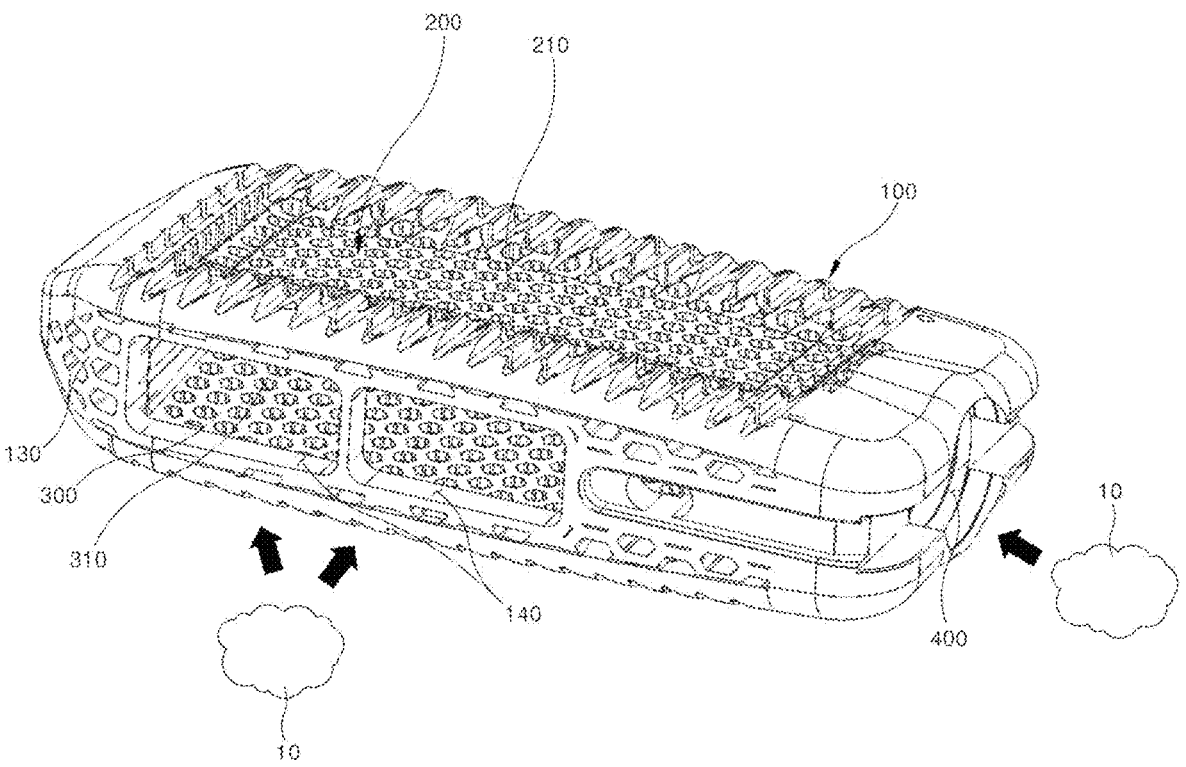
Figure 13:
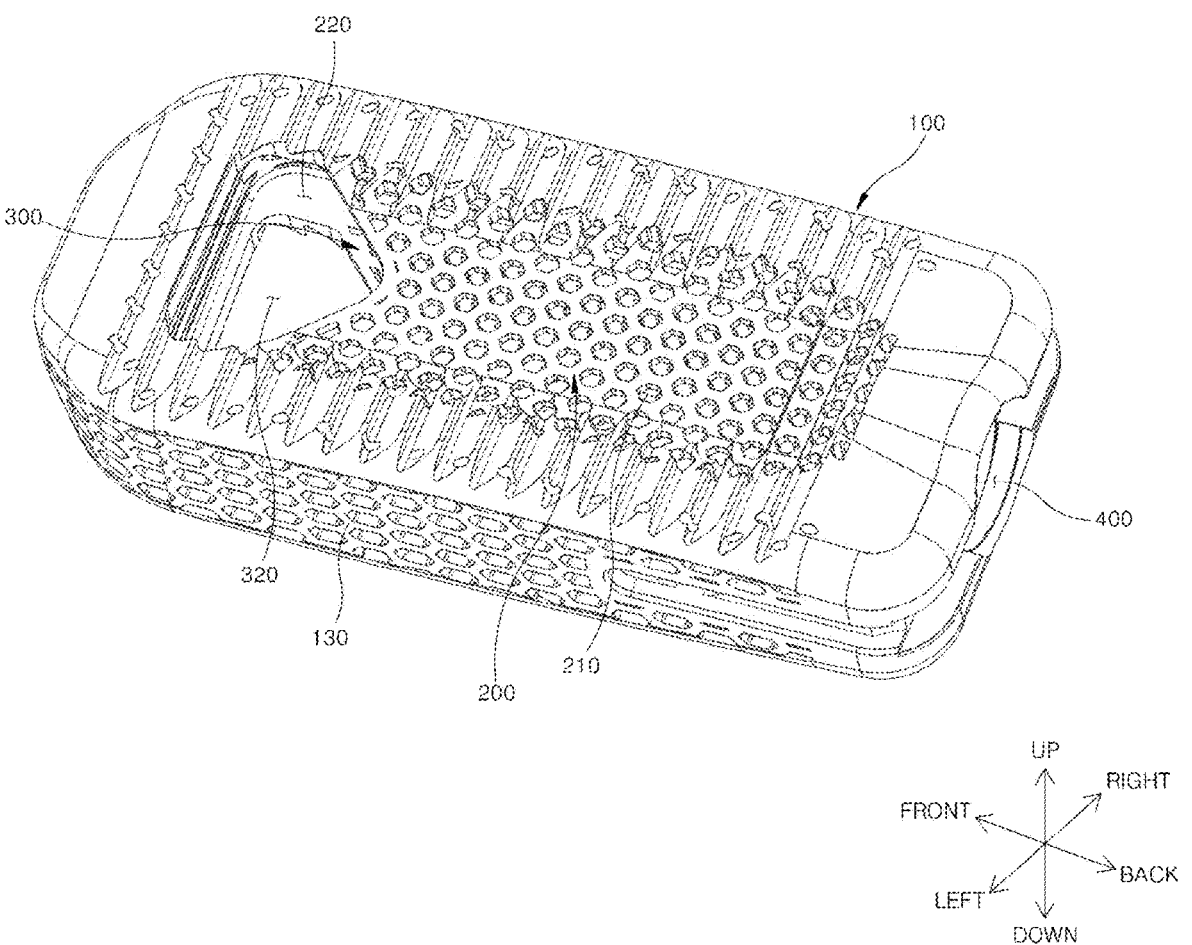
Figure 14:
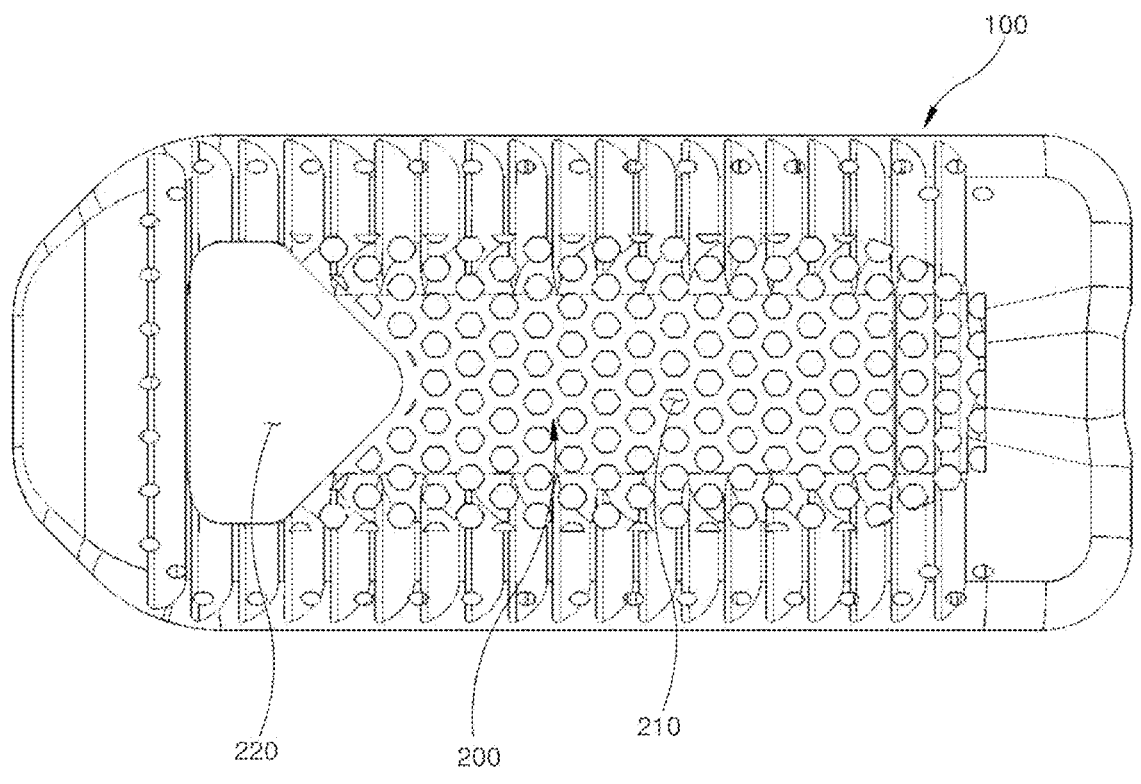
Figure 15:
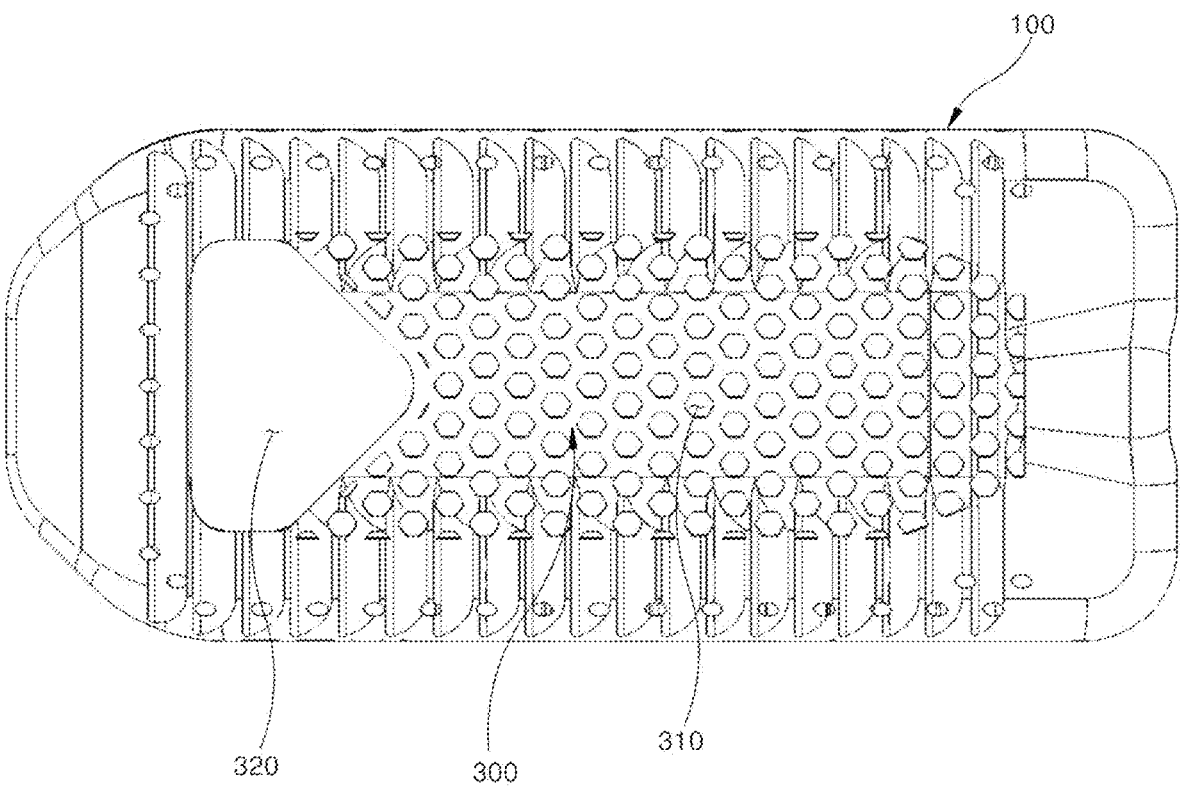
Figure 16:
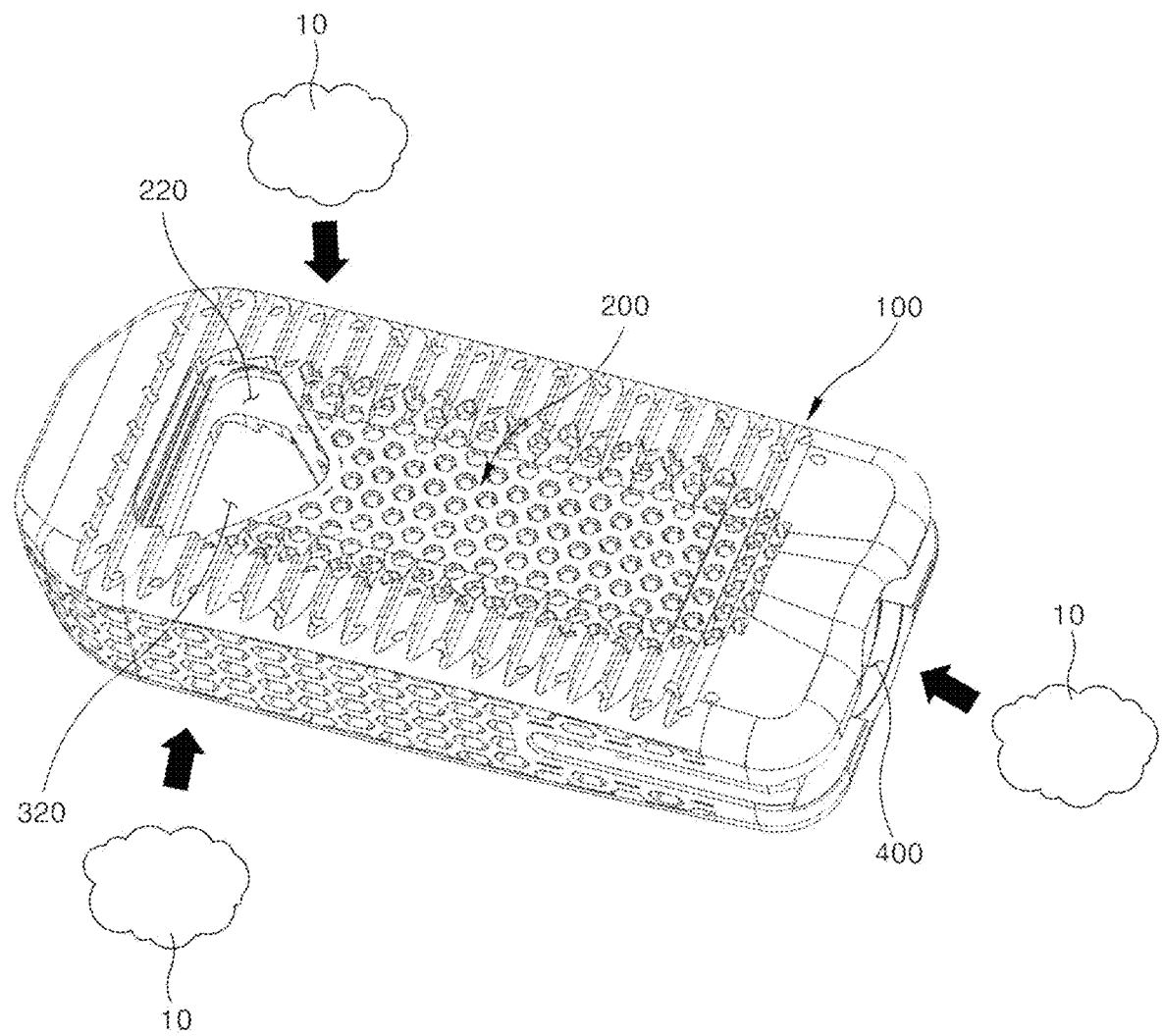
Figure 17:
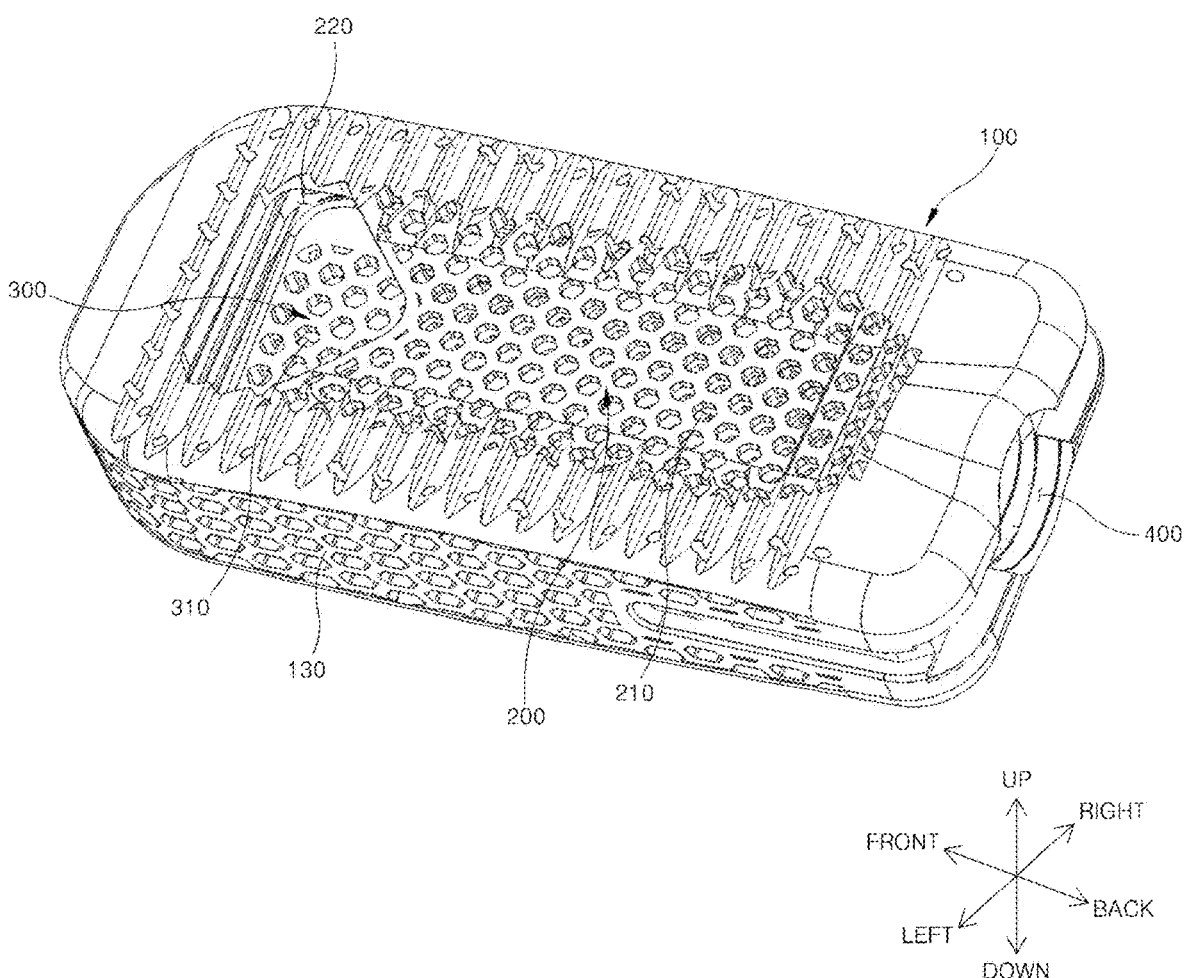
Figure 18:
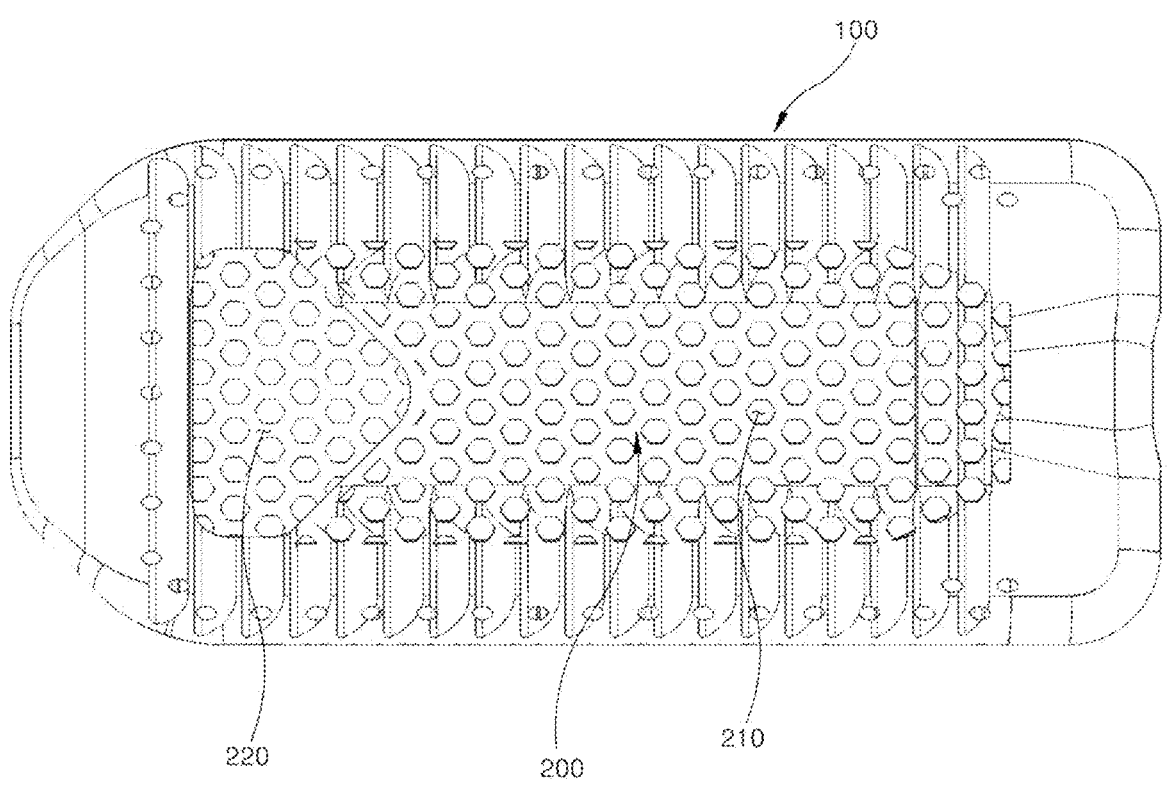
Figure 19:
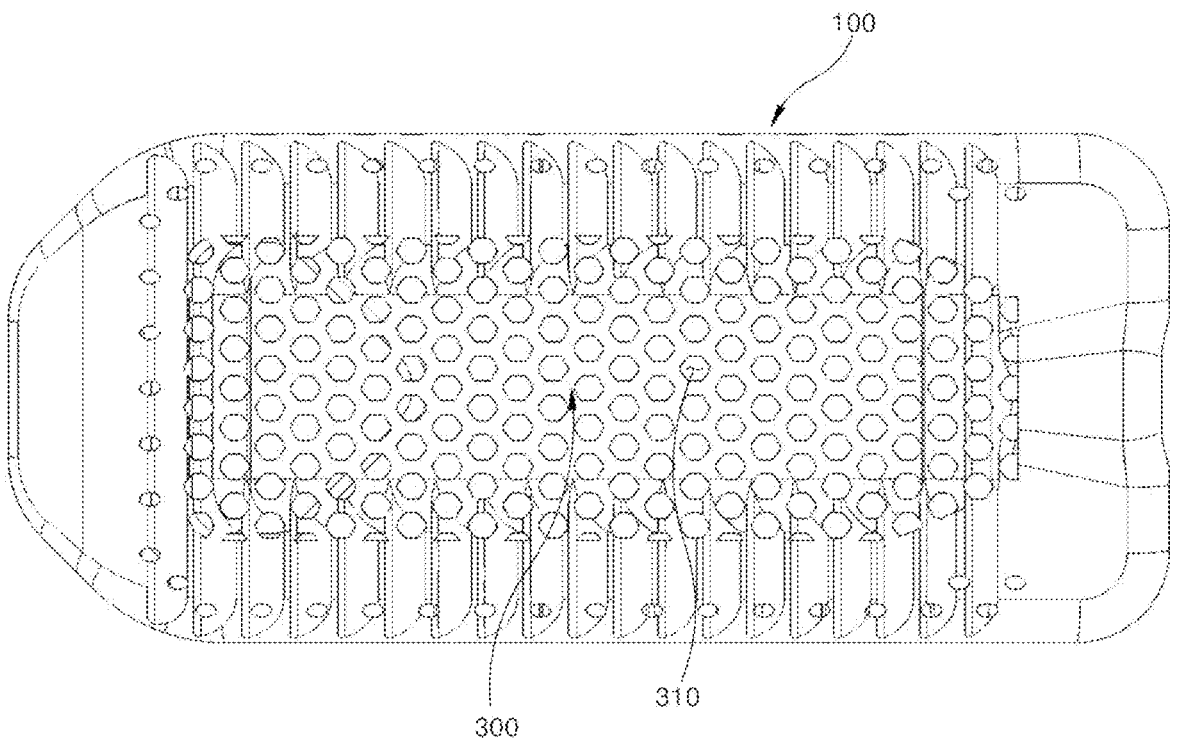
Figure 20:
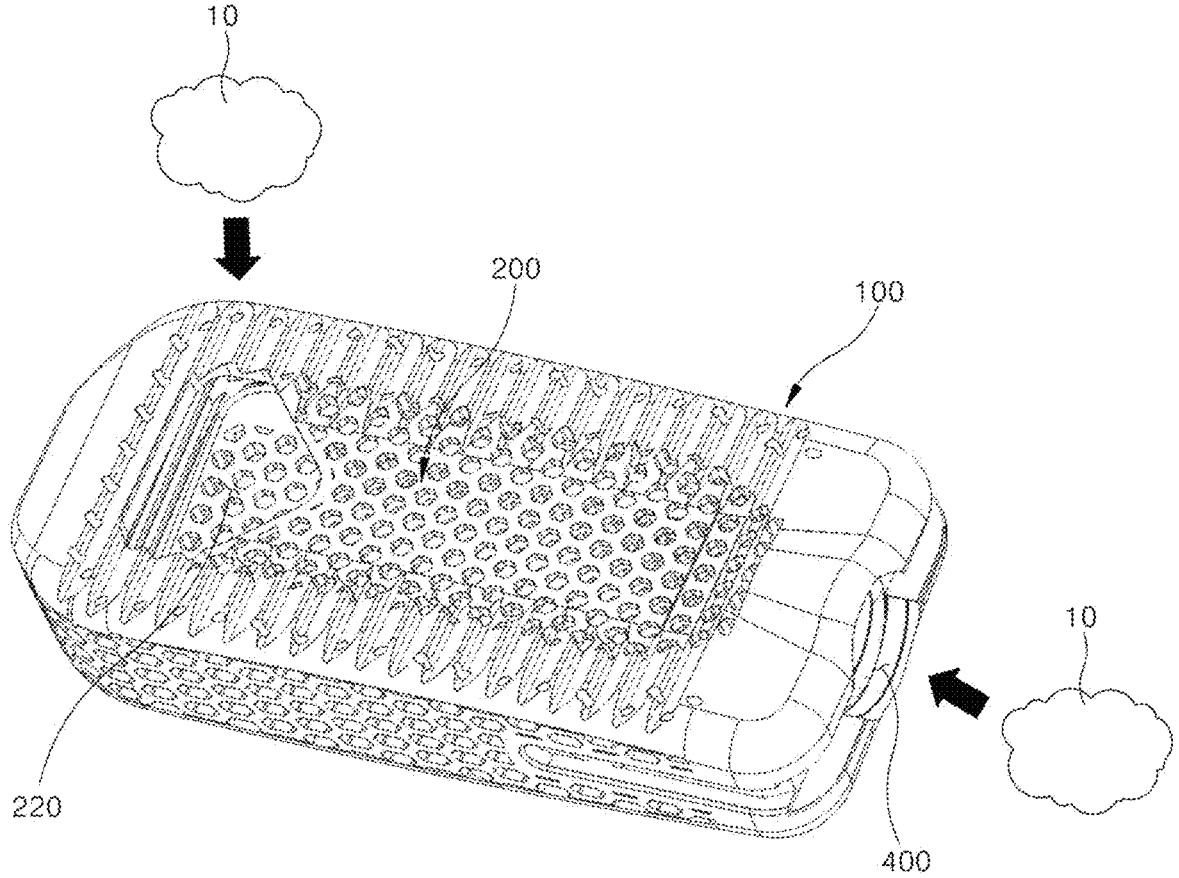
Figure 21:
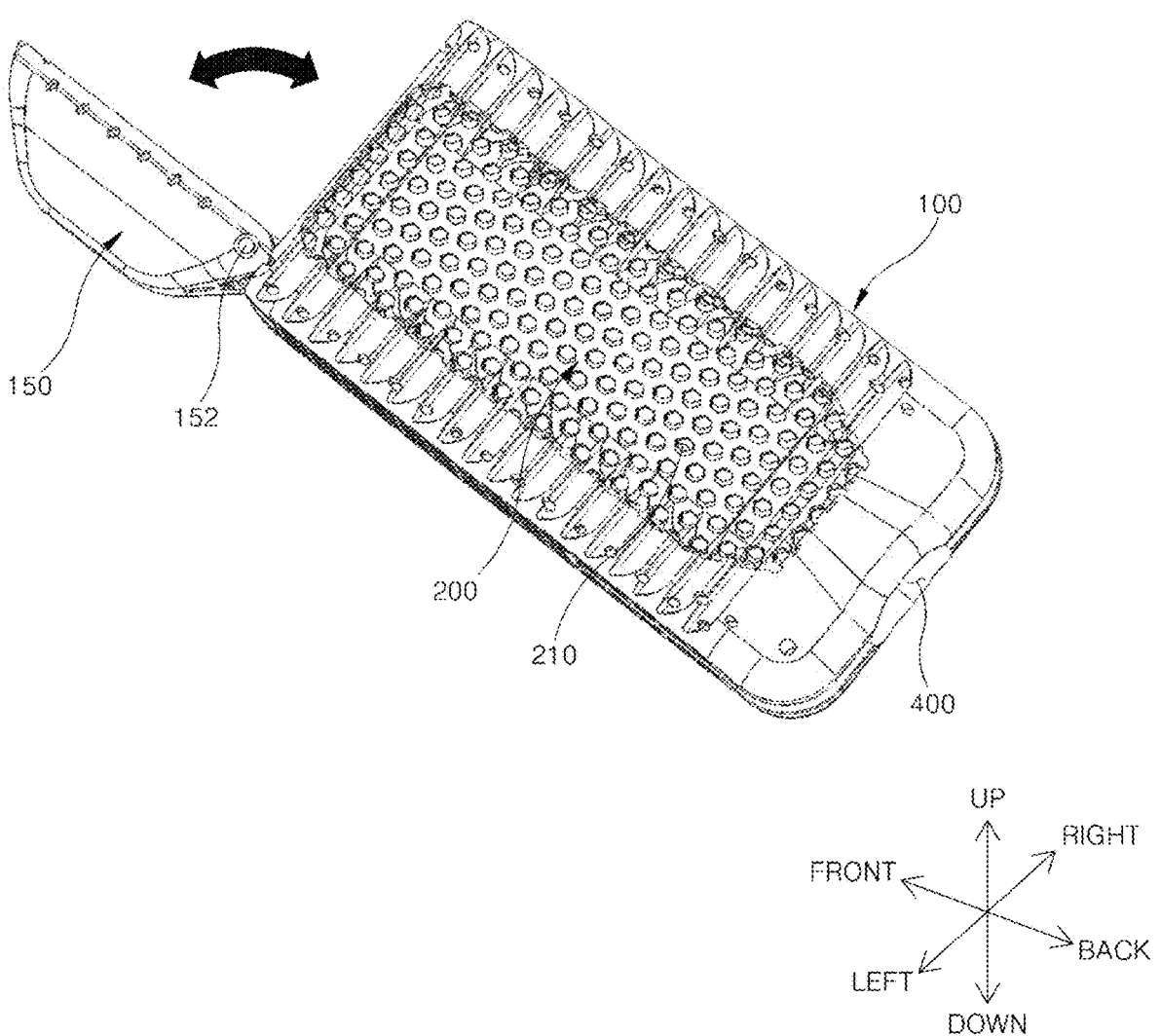
Figure 22:
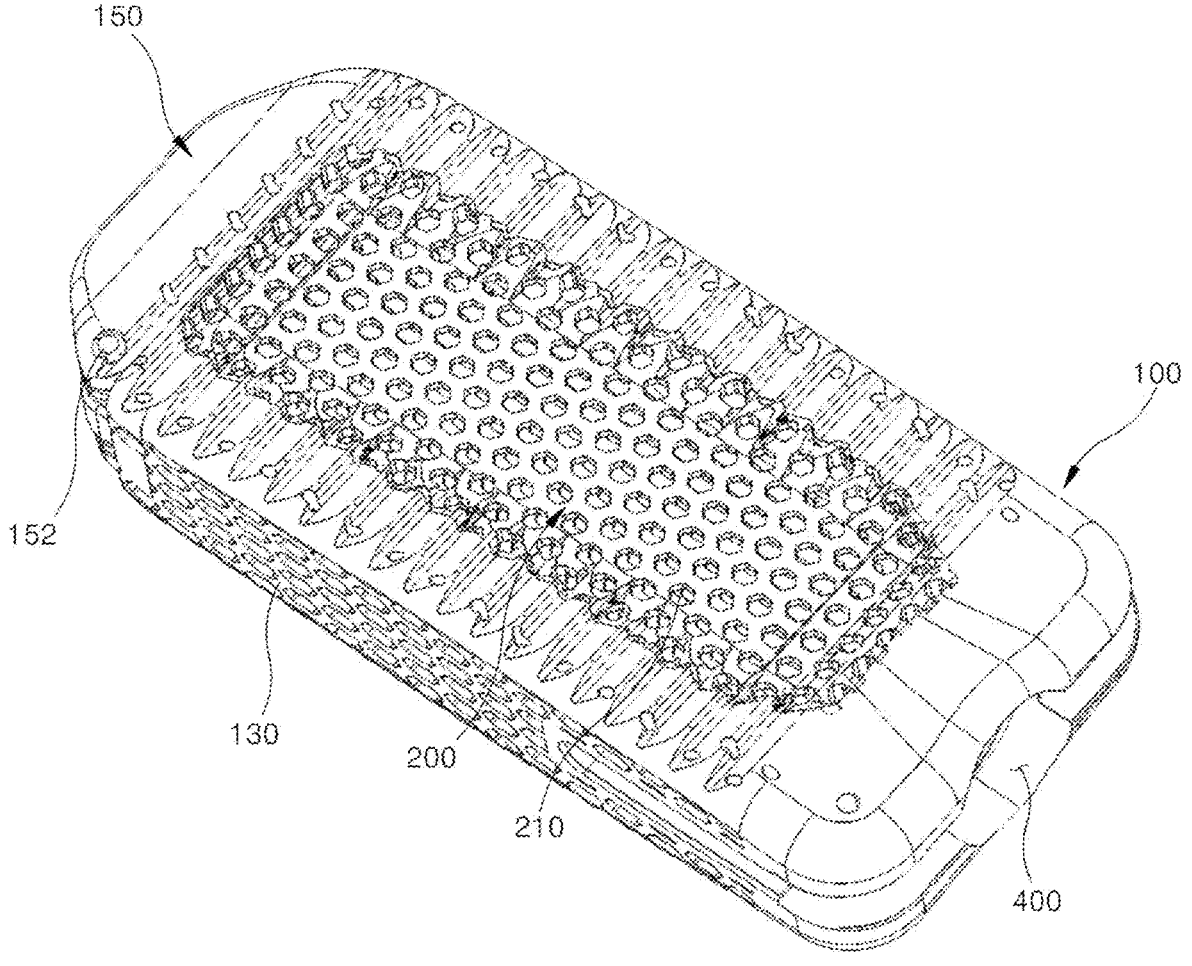
Figure 23:
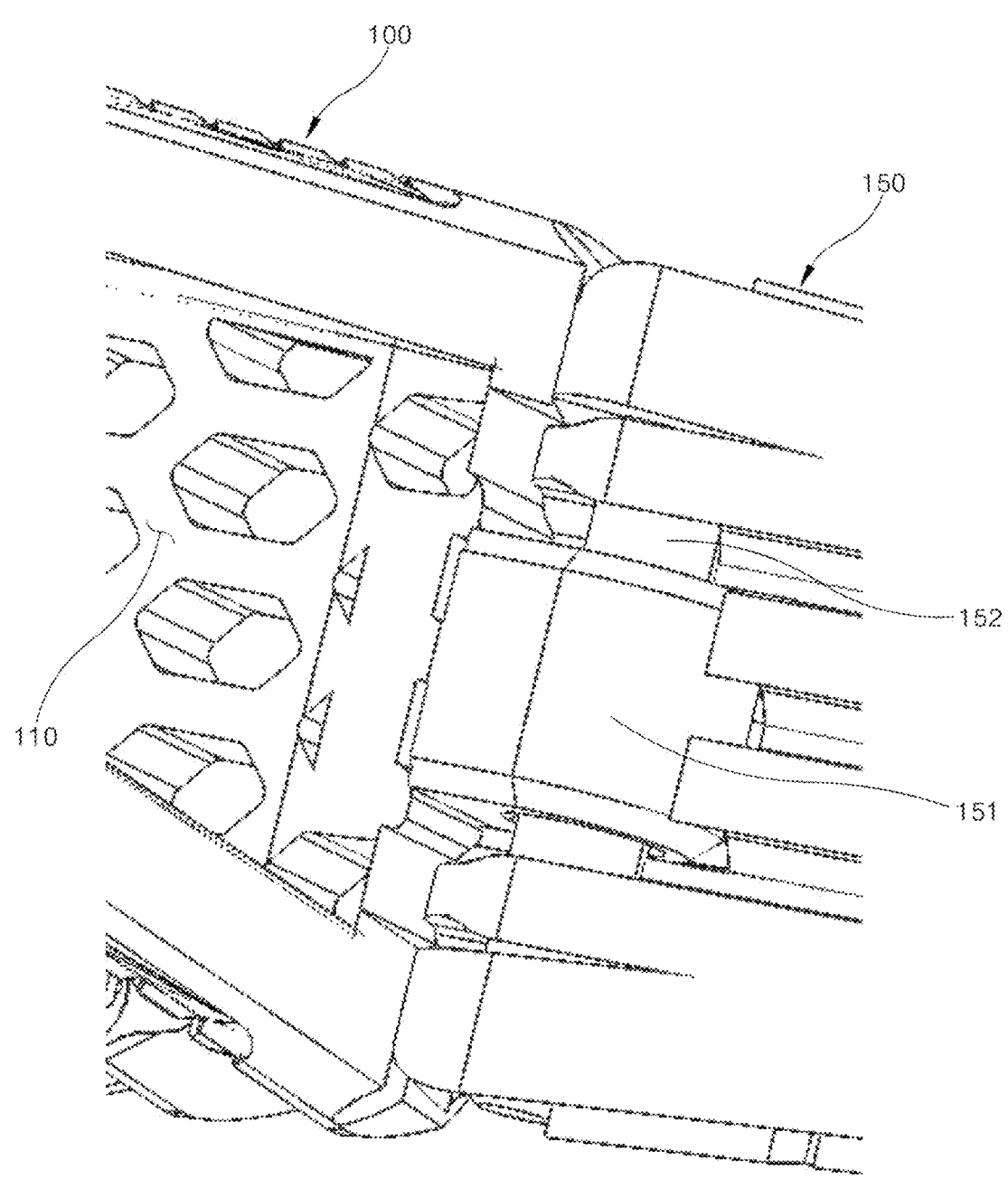
Figure 24:
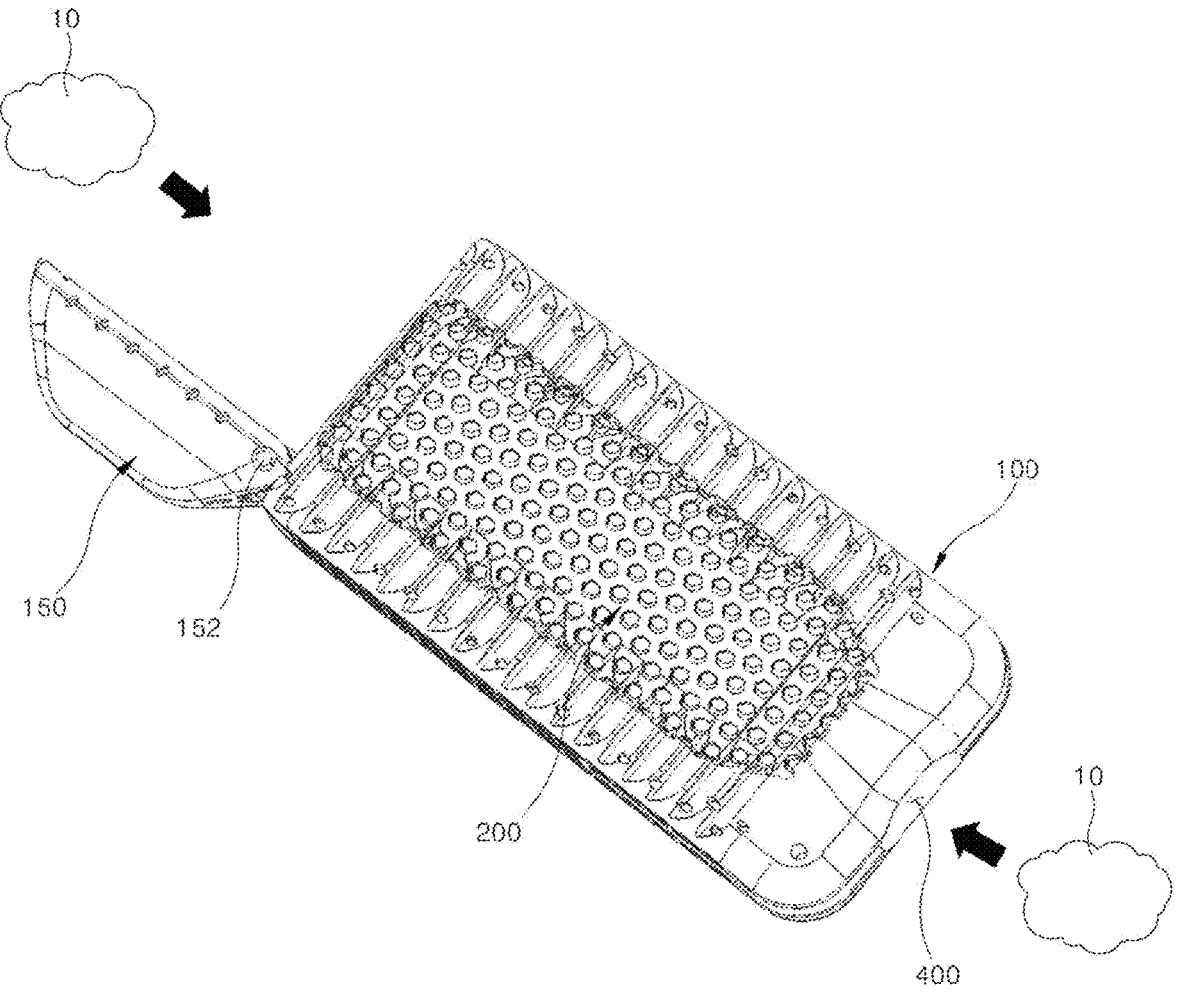
Figure 25:
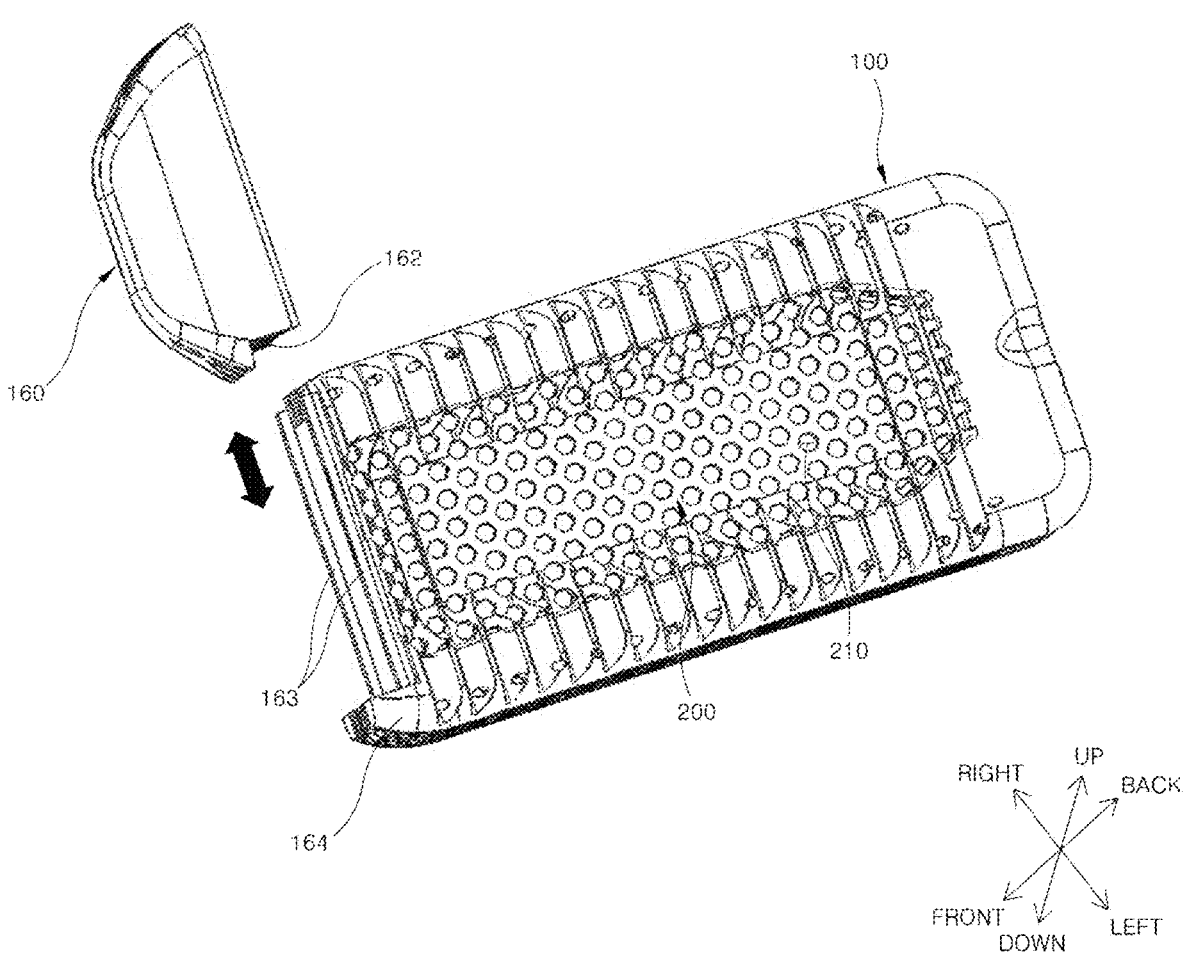
Figure 26:
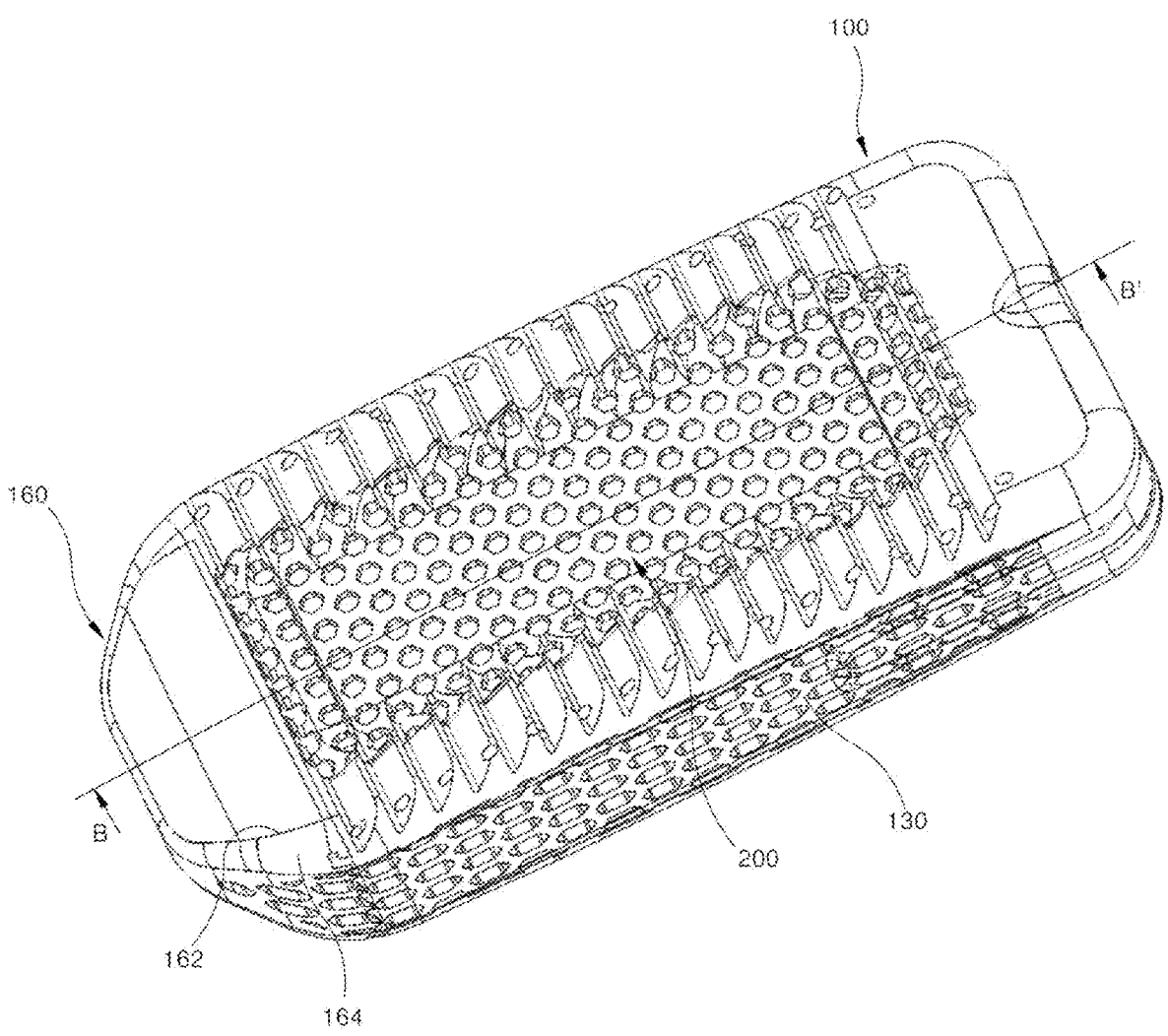
Figure 27:
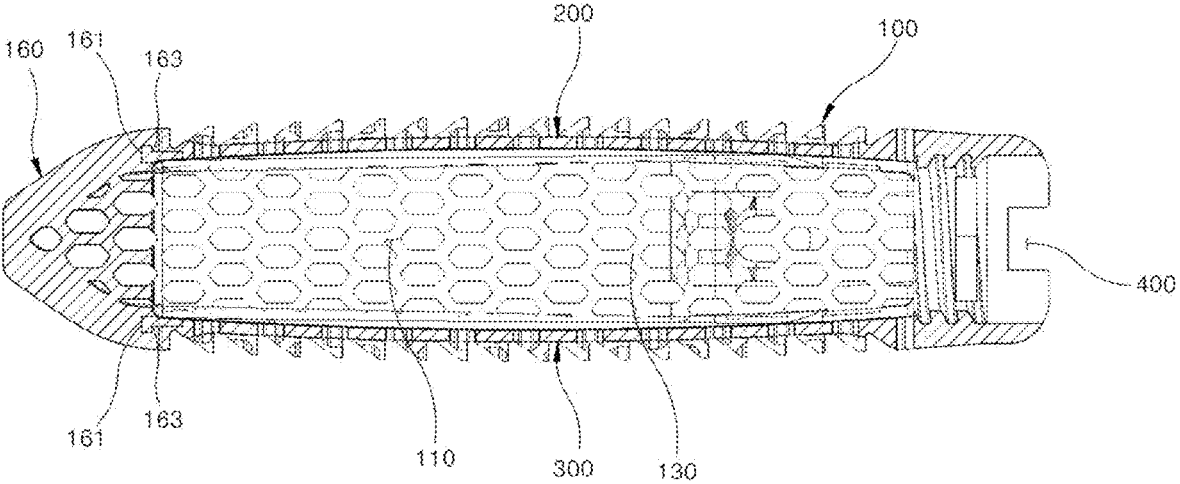
Figure 28:
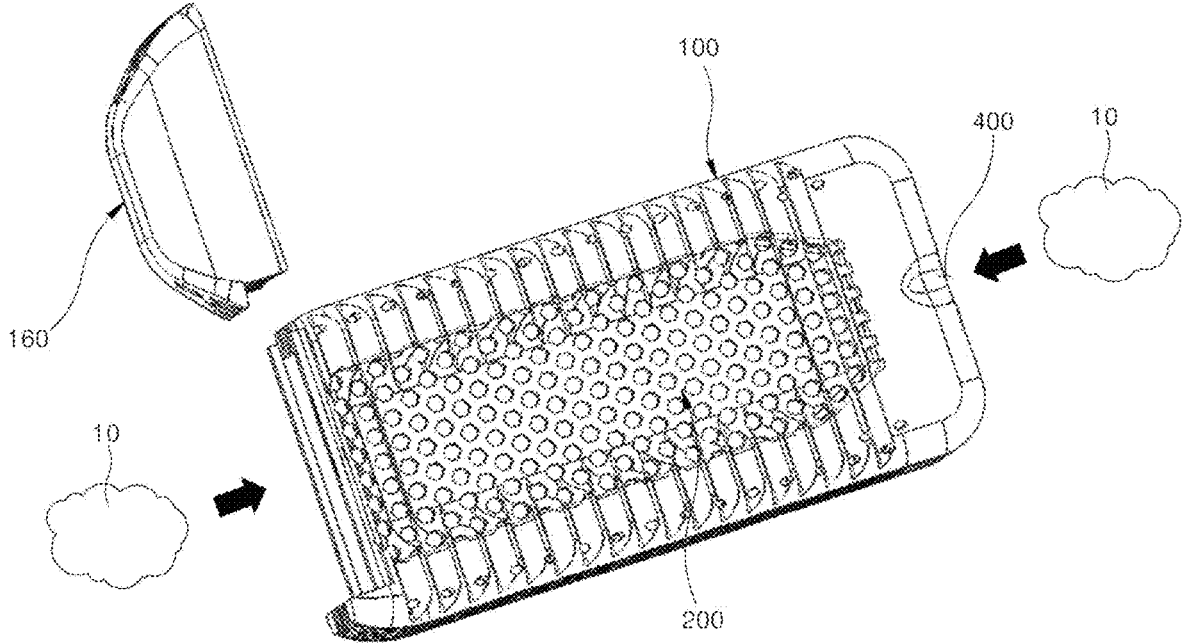
Figure 29:
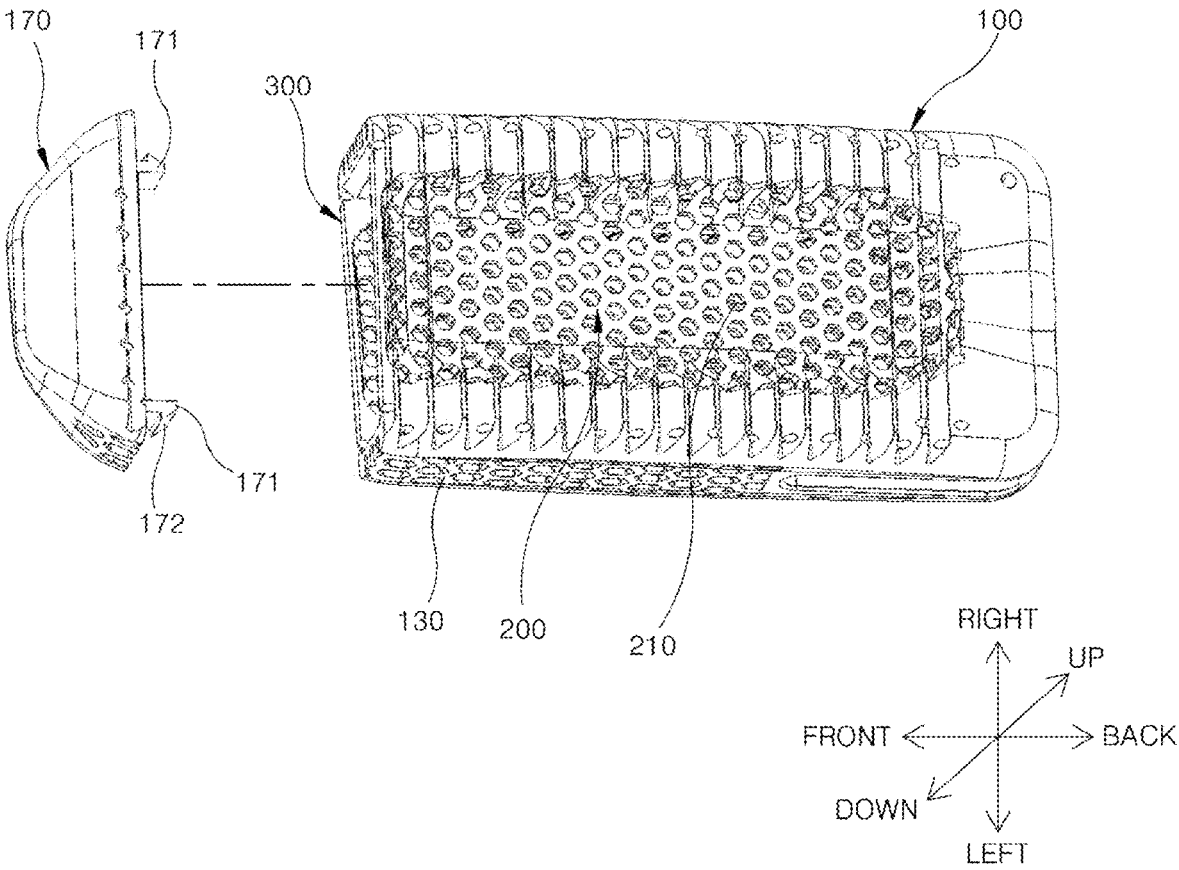
Figure 30:
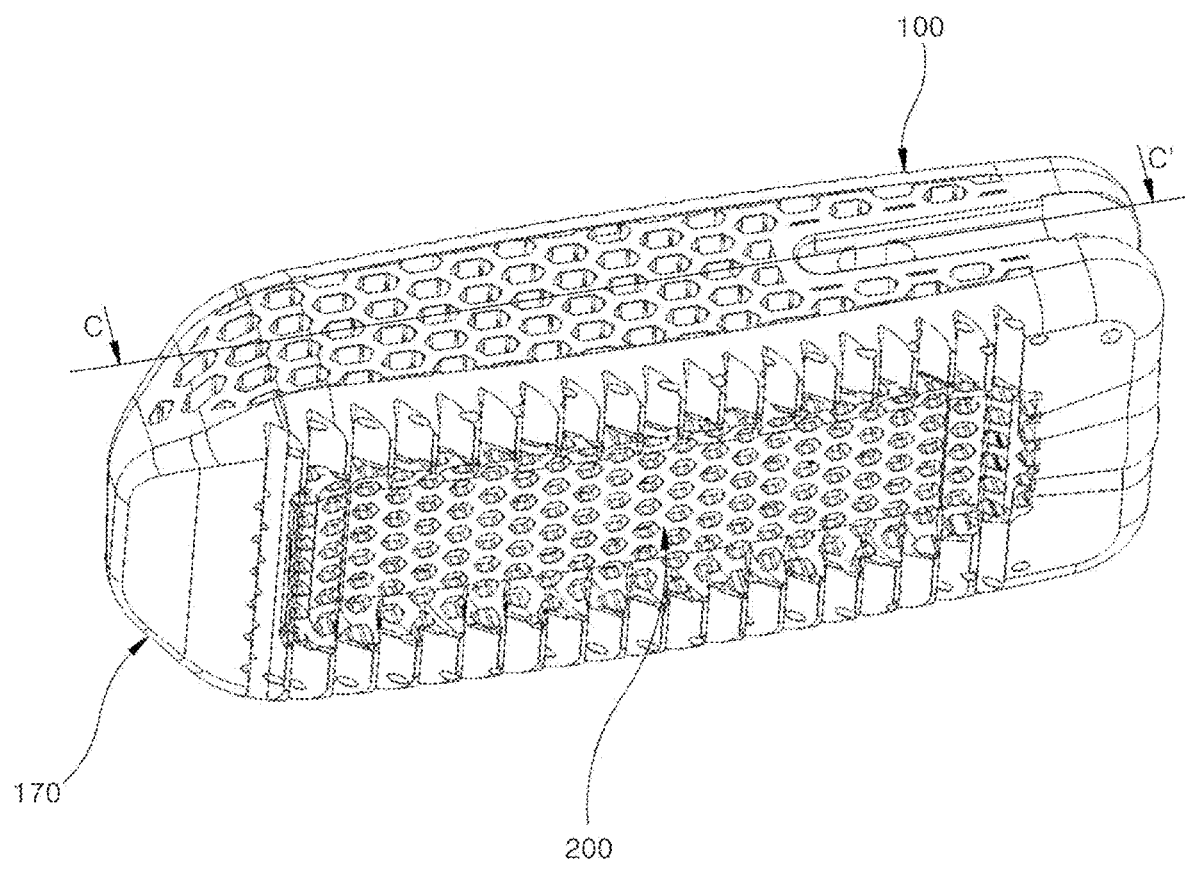
Figure 31:
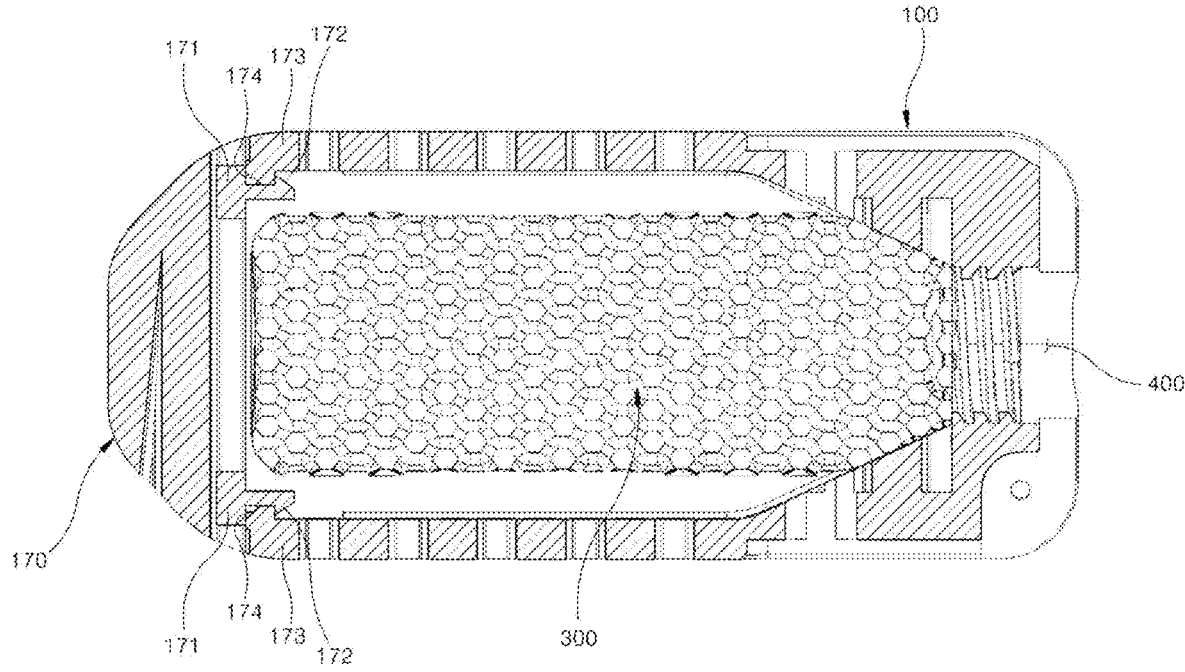
Figure 32:
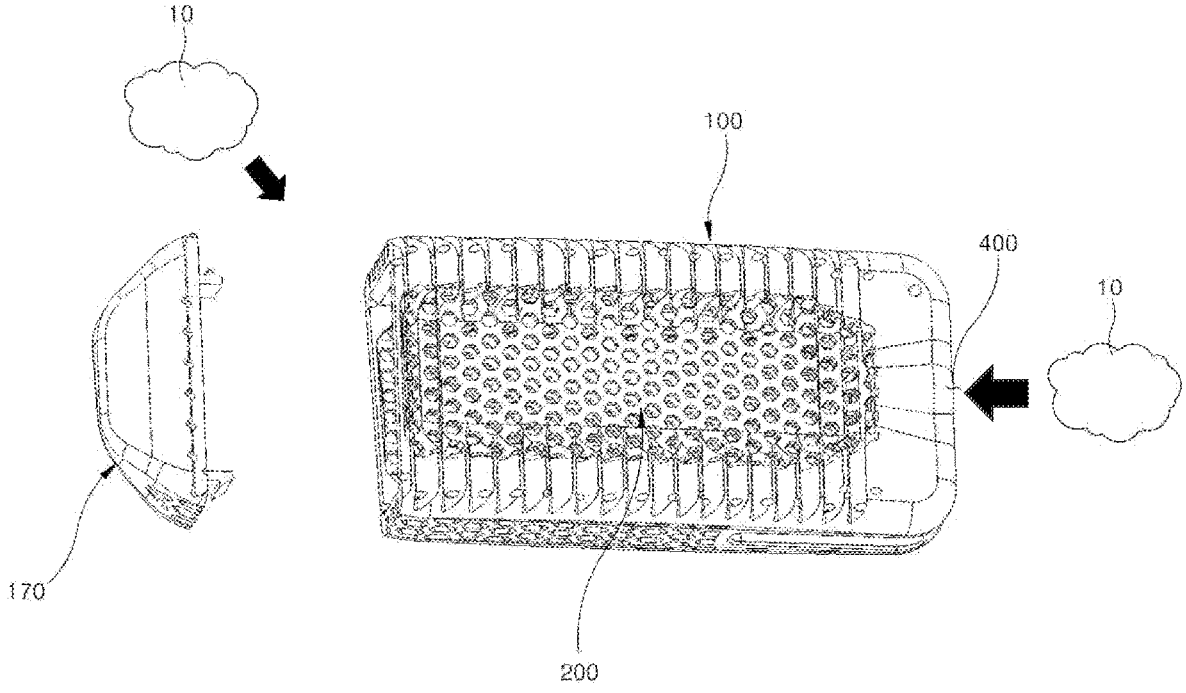
Figure 33:
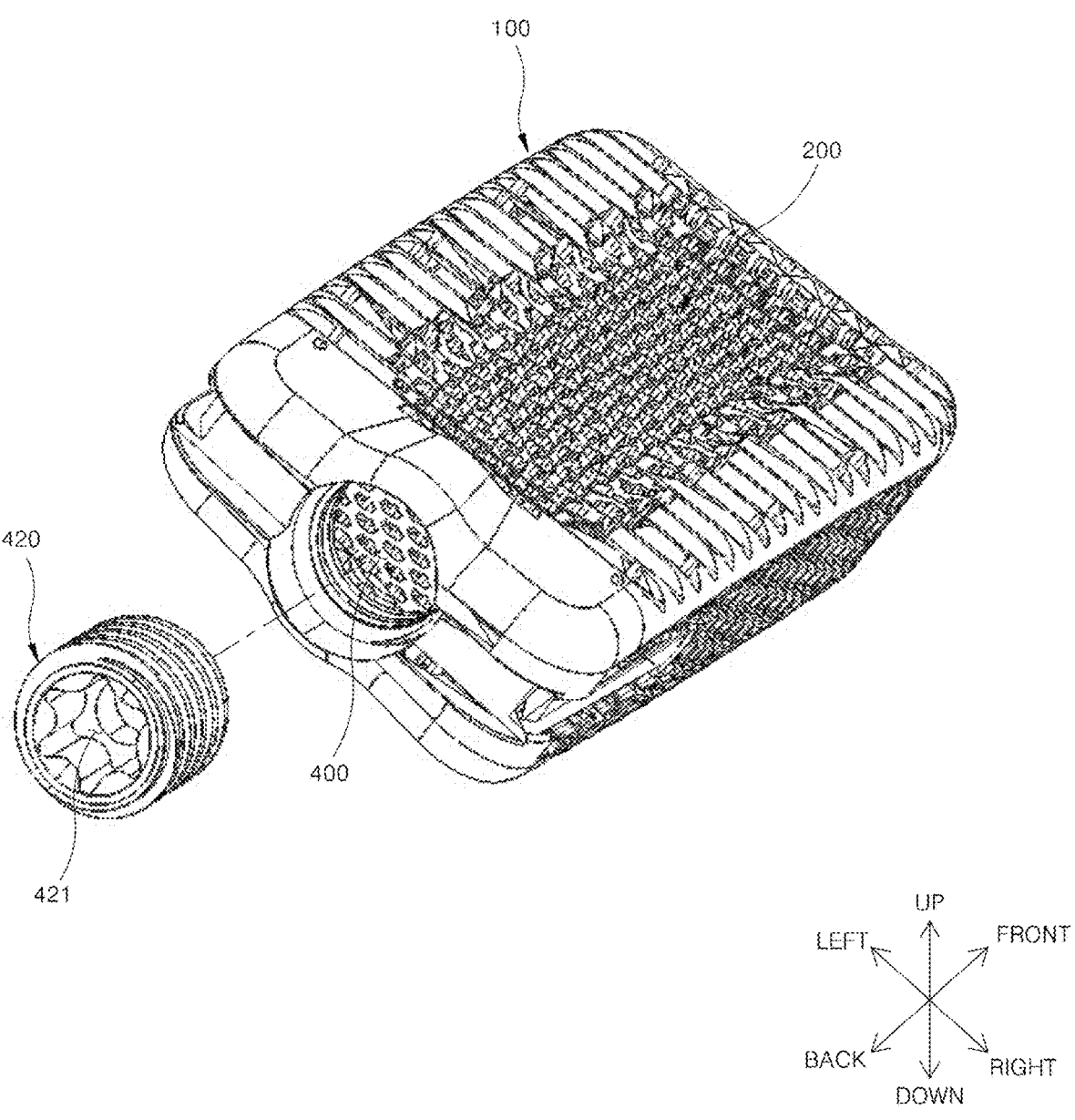
Figure 34:
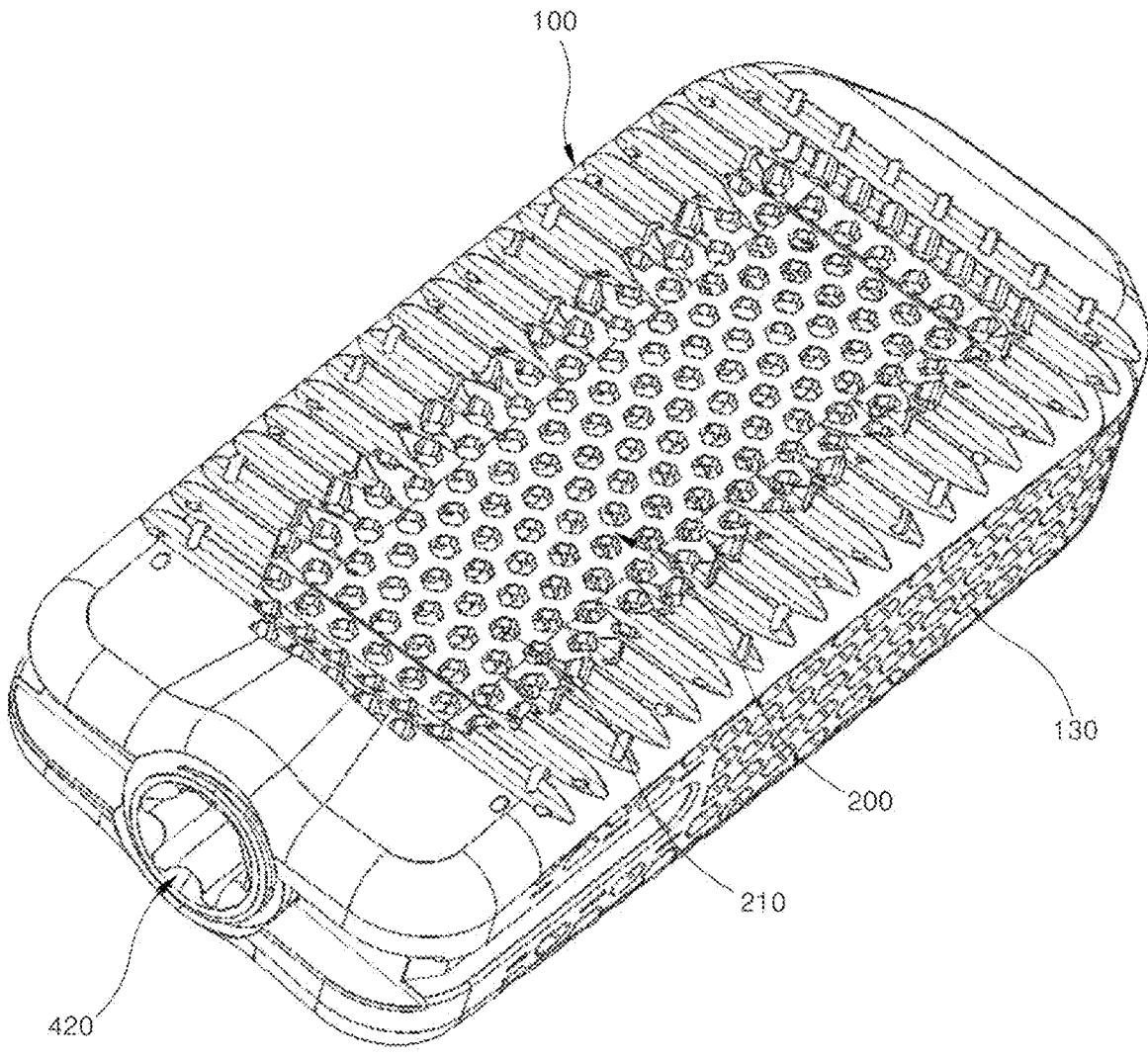
Figure 35:
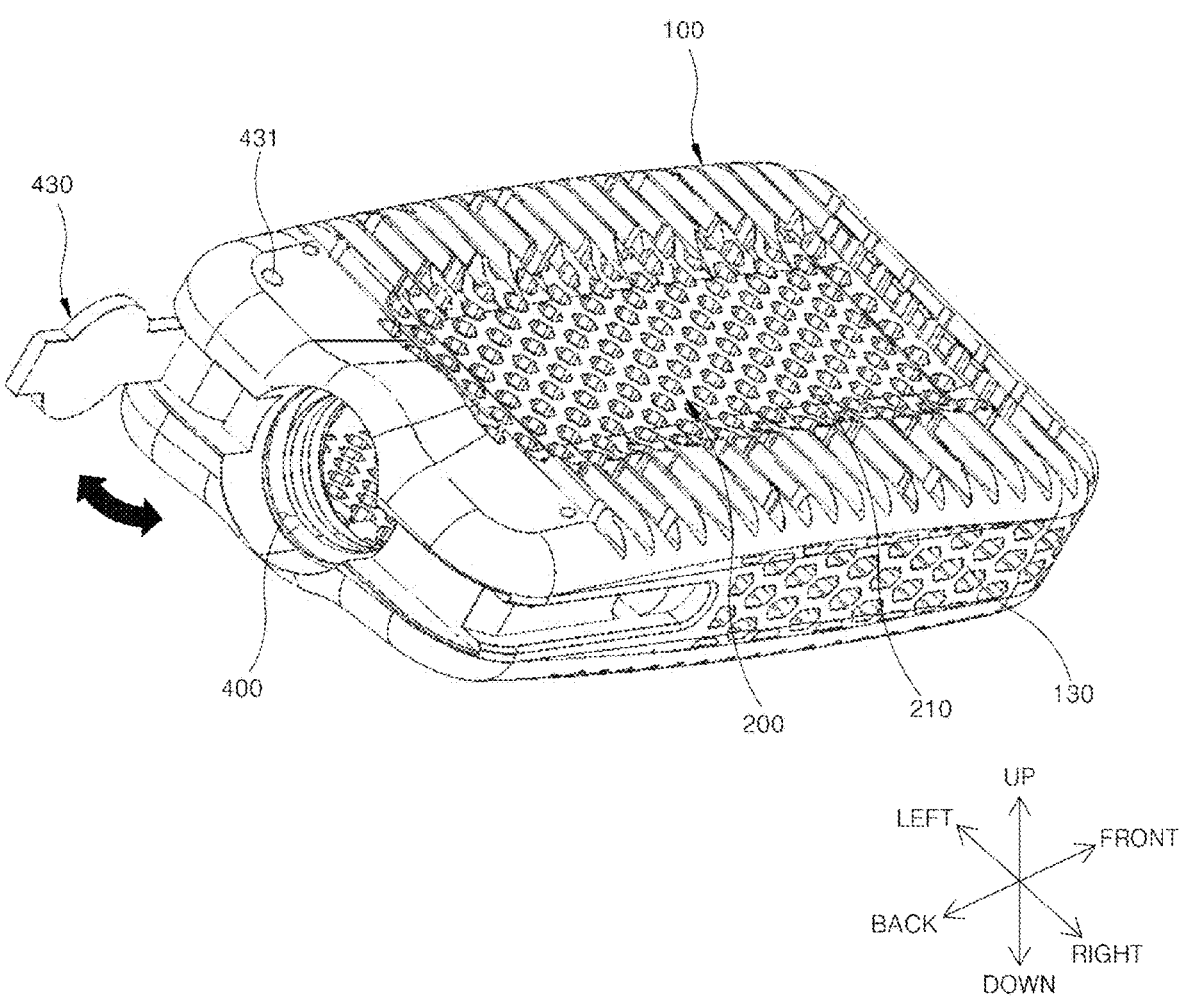
Figure 36:
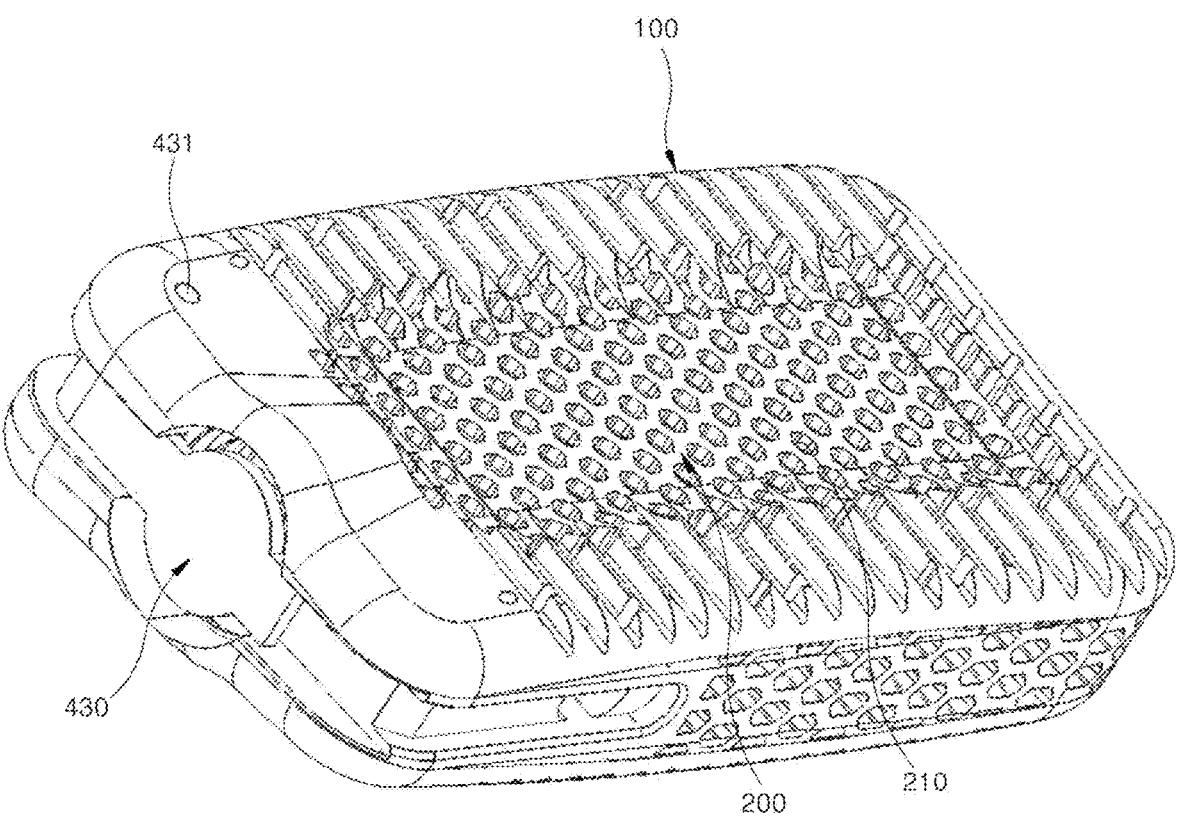
Figure 37:
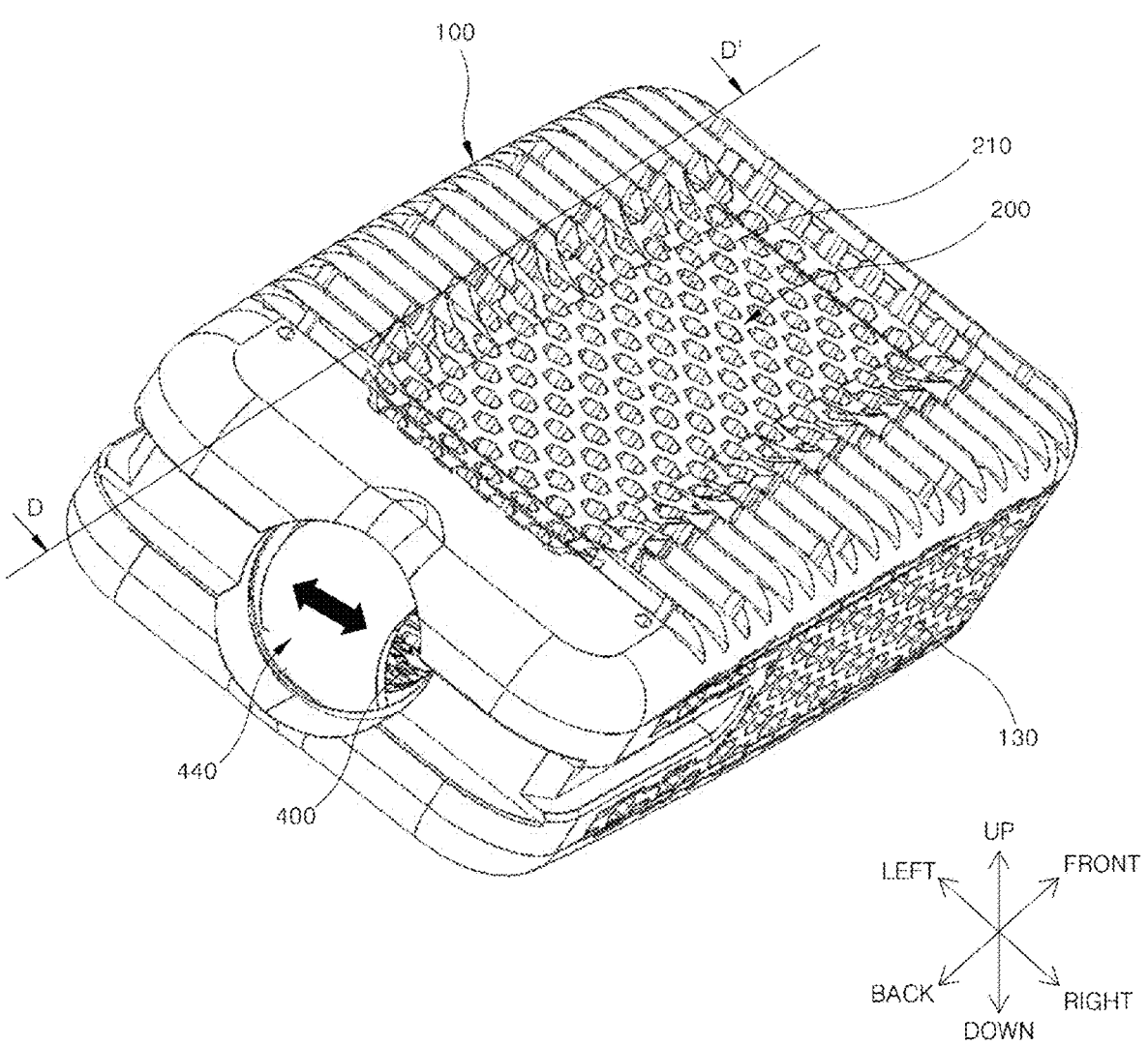
Figure 38:
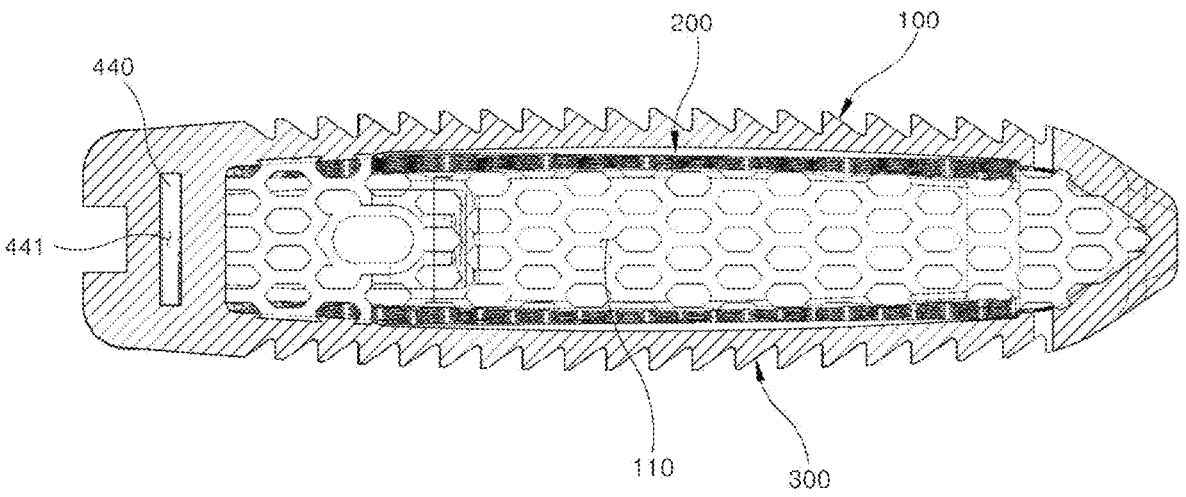

4 stood from the following detailed description taken in conjunction with the accompanying drawings, in which:

FIG. 1 is a perspective view showing the overall appearance of a box-shaped spinal cage structure according to a first embodiment of the present invention;

FIG. 2 is a plan view showing the box-shaped spinal cage structure according to the first embodiment of the present invention;

FIG. 3 is a bottom view showing the box-shaped spinal cage structure according to the first embodiment of the present invention;

FIG. 4 is a side view showing the box-shaped spinal cage structure according to the first embodiment of the present invention;

FIG. 5 is a rear view showing the box-shaped spinal cage structure according to the first embodiment of the present invention;

FIG. 6 is a cross-sectional view taken along line A-A' of FIG. 1 according to the first embodiment of the present invention;

FIG. 7 is a view showing a state of use of the box-shaped spinal cage structure according to the first embodiment of the present invention in which a bone graft is inserted into a cage body;

FIG. 8 is a view showing the state of use of the box-shaped spinal cage structure according to the first embodiment of the present invention in which the bone graft is inserted into the cage body using a device fixing unit;

FIG. 9 is a perspective view showing the overall appearance of a box-shaped spinal cage structure according to a second embodiment of the present invention;

FIG. 10 is a left side view showing the box-shaped spinal cage structure according to the second embodiment of the present invention;

FIG. 11 is a right side view showing the box-shaped spinal cage structure according to the second embodiment of the present invention;

FIG. 12 is a view showing a state of use of the box-shaped spinal cage structure according to the second embodiment of the present invention in which a bone graft is inserted into a cage body;

FIG. 13 is a perspective view showing the overall appearance of a box-shaped spinal cage structure according to a third embodiment of the present invention;

FIG. 14 is a plan view showing the box-shaped spinal cage structure according to the third embodiment of the present invention;

FIG. 15 is a bottom view showing the box-shaped spinal cage structure according to the third embodiment of the present invention;

FIG. 16 is a view showing a state of use of the box-shaped spinal cage structure according to the third embodiment of the present invention in which a bone graft is inserted into a cage body;

FIG. 17 is a perspective view showing the overall appearance of a box-shaped spinal cage structure according to a fourth embodiment of the present invention;

FIG. 18 is a plan view showing the box-shaped spinal cage structure according to the fourth embodiment of the present invention;

FIG. 19 is a bottom view showing the box-shaped spinal cage structure according to the fourth embodiment of the present invention;

FIG. 20 is a view showing a state of use of the box-shaped spinal cage structure according to the fourth embodiment of the present invention in which a bone graft is inserted into a cage body;

FIG. 21 is a view showing an opened state of a front rotating part of a box-shaped spinal cage structure according to a fifth embodiment of the present invention;

FIG. 22 is a view showing a closed state of the front rotating part according to the fifth embodiment of the present invention;

FIG. 23 is an enlarged view of a coupling portion of the front rotating part according to the fifth embodiment of the present invention;

FIG. 24 is a view showing a state of use of the box-shaped spinal cage structure according to the fifth embodiment of the present invention in which a bone graft is inserted into a cage body;

FIG. 25 is a view showing an opened state of a front sliding part of a box-shaped spinal cage structure according to a sixth embodiment of the present invention;

FIG. 26 is a view showing a closed state of the sliding part according to the sixth embodiment of the present invention;

FIG. 27 is a cross-sectional view taken along line B-B' of FIG. 26 according to the sixth embodiment of the present invention;

FIG. 28 is a view showing a state of use of the box-shaped spinal cage structure according to the sixth embodiment of the present invention in which a bone graft is inserted into a cage body;

FIG. 29 is a view showing an opened state of a front locking part of a box-shaped spinal cage structure according to a seventh embodiment of the present invention;

FIG. 30 is a view showing a closed state of the front locking part according to the seventh embodiment of the present invention;

FIG. 31 is a cross-sectional view taken along line C-C' of FIG. 30 according to the seventh embodiment of the present invention;

FIG. 32 is a view showing a state of use of the box-shaped spinal cage structure according to the seventh embodiment of the present invention in which a bone graft is inserted into a cage body;

FIG. 33 is a view showing a separated state of a set screw of a box-shaped spinal cage structure according to an eighth embodiment of the present invention;

FIG. 34 is a view showing a fastened state of the set screw according to the eighth embodiment of the present invention;

FIG. 35 is a view showing an opened state of a rear rotating part of a box-shaped spinal cage structure according to a ninth embodiment of the present invention;

FIG. 36 is a view showing a closed state of the rear rotating part according to the ninth embodiment of the present invention;

FIG. 37 is a view showing a closed of a rear movable part of a box-shaped spinal cage structure according to a tenth embodiment of the present invention; and FIG. 38 is a cross-sectional view taken along line D-D' of FIG. 37 according to the tenth embodiment of the present invention.

DETAILED DESCRIPTION OF THE INVENTION

Hereinafter, the present invention will be described detail based on the accompanying drawings to fully convey the scope of the present invention to those skilled in the art to which the present invention pertains. However, the present invention may be implemented in many different forms and is not limited to the embodiments described herein.

In order to clearly explain the present invention, parts that are not relevant to the description will be omitted, and the same or similar components will be indicated by the same reference numerals throughout the description.

In addition, terms or words used in the description and the claims should not be construed as limited to their usual or dictionary meanings, and should be interpreted as having meanings and concepts consistent with the technical idea of the present invention based on the principle in which an inventor may appropriately define the concept of a term to explain his or her invention in the best way.

FIG. 1 is a perspective view showing the overall appearance of a box-shaped spinal cage structure according to a first embodiment of the present invention, FIG. 2 is a plan view showing the box-shaped spinal cage structure according to the first embodiment of the present invention, FIG. 3 is a bottom view showing the box-shaped spinal cage structure according to the first embodiment of the present invention, FIG. 4 is a side view showing the box-shaped spinal cage structure according to the first embodiment of the present invention, FIG. 5 is a rear view showing the box-shaped spinal cage structure according to the first embodiment of the present invention, FIG. 6 is a cross-sectional view taken along line A-A' of FIG. 1 according to the first embodiment of the present invention, FIG. 7 is a view showing a state of use of the box-shaped spinal cage structure according to the first embodiment of the present invention in which a bone graft is inserted into a cage body, and FIG. 8 is a view showing the state of use of the box-shaped spinal cage structure according to the first embodiment of the present invention in which the bone graft is inserted into the cage body using a device fixing unit.

As shown in these figures, the box-shaped spinal cage structure according to the first embodiment of the present invention includes a cage body 100, an upper blocking part 200, a lower blocking part 300, and a rear insertion hole 400.

The cage body 100 is a medical device used for spinal fusion surgery, and is inserted between vertebral bodies to maintain a distance between the vertebral bodies and to secure a space into which the bone enters and grows for fusion.

An internal space 110 is formed in the center of the cage body 100, and the internal space 110 is filled with a bone graft 10 including autograft, allograft, or synthetic bone to promote bone growth.

The cage body 100 may include a polymer material as a main component of the cage body 100, and in addition, various additives or filling materials may be added thereto.

Here, the polymer material forming the cage body 100 may basically be titanium or a titanium alloy material with excellent biocompatibility, and a material, such as polyether ether ketone (PEEK), may be used depending on user's needs.

Although, in the illustrated embodiment, the cage body 100 is formed in a long rectangular shape extending forward and rearward, the cage body 100 is not limited thereto and may be formed in various shapes, such as a flat shape, a curved shape, a disc shape, etc. The cage body 100 may be manufactured in a 3D printer using Selective Laser Melting (SLM).

A plurality of teeth 12 that penetrates an upper vertebral body and a lower vertebral body to enable the cage body 100 to have a certain fixing force between the vertebral bodies is formed on the upper and lower surfaces of the cage body 100. The plurality of teeth 120 stably maintain the position of the cage body 100 in the initial stage of a spinal fusion procedure.

The upper blocking part 200 is coupled to the upper surface of the cage body 100 to block the internal space 110 of the cage body 100 from the outside, and the lower blocking part 300 is coupled to the lower surface of the cage body 100 to block the internal space of the cage body 100 from the outside.

That is, both the upper and lower surfaces of the cage body 100 are blocked, and may thus maximally prevent the bone graft 10 filling the inside of the cage body 100 from being lost during a process of inserting the cage body 100 into the human body.

As shown in FIG. 2, a plurality of upper pores 210 is perforated in the upper blocking part 200 in the upward and downward directions, and as shown in FIG. 3, a plurality of lower pores 310 is perforated in the lower blocking part 300 in the upward and downward directions.

Although, in the illustrated embodiment, the upper pores 210 and the lower pores 310 are formed in a hexagonal shape, the upper pores 210 and the lower pores 310 are not limited thereto and may be formed regularly or irregularly in various shapes.

As shown in FIG. 4, a plurality of left and right structures 130 having a hollow interior is stacked on both side surfaces of the cage body 100. Although, in the illustrated example, the left and right structures 130 are formed in the form of a hollow column having a hexagonal cross-section and a predetermined width, the left and right structures 130 are not limited thereto. As such, in the present invention, since the upper pores 210 are formed in the upper blocking part 200, the lower pores 310 are formed in the lower blocking part 300, and the plurality of left and right structures 130 having the hollow interior is formed on both side surfaces of the cage body 100, pores are formed on the upper, lower, left and right sides of the cage body 100, and thereby, the cage body 100 is advantageous for bone growth through the pores and may improve a fusion rate.

As shown in FIG. 5, the rear insertion hole 400 is formed through the rear surface of the cage body 100, and the bone graft 10 is inserted into the internal space 110 of the cage body 100 through the rear insertion hole 400.

The rear insertion hole 400 has a diameter that is relatively larger than the diameter of the upper pores 210, the diameter of the lower pores 310, and the size of the hollow spaces inside the left and right structures 130. In the embodiment of the present invention, the rear insertion hole 400 may have a diameter of at least 3 mm.

As shown in FIG. 8, the box-shaped spinal cage structure according to the first embodiment of the present invention may further include a device fixing unit 410 and an impactor 411 to densely fill the internal space 110 of the cage body 100 with the bone graft 10. The device fixing unit 410 is inserted into the rear insertion hole 400 of the cage body 100, and the bone graft 10 is accommodated in the device fixing unit 410. The device fixing unit 410 is formed in a shape similar to a funnel configured such that the diameter of a part thereof inserted into the rear insertion hole 400 is smaller than the diameter of the rear part thereof.

The impactor 411 enters the inside of the device fixing unit 410 to insert the bone graft 10 accommodated in the device fixing unit 410 into the internal space 110 of the cage body 100, and the internal space 110 of the cage body 100 may be filled with the bone graft 10 by continuously pressing the bone graft 10 using the impactor 411.

FIG. 9 is a perspective view showing the overall appearance of a box-shaped spinal cage structure according to a second embodiment of the present invention, FIG. 10 is a left side view showing the box-shaped spinal cage structure according to the second embodiment of the present invention, FIG. 11 is a right side view showing the box-shaped spinal cage structure according to the second embodiment of the present invention, and FIG. 12 is a view showing a state of use of the box-shaped spinal cage structure according to the second embodiment of the present invention in which a bone graft is inserted into a cage body.

In the same manner as the first embodiment of the present invention, the box-shaped spinal cage structure according to the second embodiment of the present invention includes a cage body 100, an upper blocking part 200, a lower blocking part 300, and a rear insertion hole 400.

A plurality of upper pores 210 is perforated in the upper blocking part 200 in the upward and downward directions, a plurality of lower pores 310 is perforated in the lower blocking part 300 in the upward and downward directions, and a plurality of left and right structures 130 having a hollow interior is stacked on both side surfaces of the cage body 100. Here, side windows 140 having a larger size than the size of the hollow interiors of the left and right structures 130 are formed in the left side surface of the cage body 100 according to the second embodiment of the present invention by cutting. Although, in the illustrated embodiment, the side windows 140 are provided as a pair, the side windows 140 are not limited thereto.

A plurality of left and right structures 130 having a hollow interior is stacked on the right side surface of the cage body 100, in the same manner as the first embodiment of the present invention.

Since the bone graft 10 according to the first embodiment of the present invention described above is inserted into the internal space 110 of the cage body 100 only through the rear insertion hole 400, it may be difficult for the bone graft 10 to be inserted sufficiently into the inner region of the internal space 110.

As shown in FIG. 12, the second embodiment of the present invention serves to address this problem, and the bone graft 10 may be inserted into the internal space 110 of the cage body 100 through the side windows 140 and the rear insertion hole 400.

Since the bone graft 10 inserted through the side windows 140 may be directly inserted through the side surface of the cage body 100, it may be easily inserted into the inner region of the internal space 110.

FIG. 13 is a perspective view showing the overall appearance of a box-shaped spinal cage structure according to a third embodiment of the present invention, FIG. 14 is a plan view showing the box-shaped spinal cage structure according to the third embodiment of the present invention, FIG. 15 is a bottom view showing the box-shaped spinal cage structure according to the third embodiment of the present invention, and FIG. 16 is a view showing a state of use of the box-shaped spinal cage structure according to the third embodiment of the present invention in which a bone graft is inserted into a cage body.

In the same manner as the first and second embodiments of the present invention, the box-shaped spinal cage structure according to the third embodiment of the present invention includes a cage body 100, an upper blocking part 200, a lower blocking part 300, and a rear insertion hole 400.

A plurality of upper pores 210 is perforated in the upper blocking part 200 in the upward and downward directions, a plurality of lower pores 310 is perforated in the lower blocking part 300 in the upward and downward directions, and a plurality of left and right structures 130 having a hollow interior is stacked on both side surfaces of the cage body 100.

Here, as shown in FIG. 14, at least one upper window 220 having a larger size than the diameter of the plurality of upper pores 210 is formed in the front portion of the upper blocking part 200 according to the third embodiment of the present invention by cutting.

In addition, as shown in FIG. 15, at least one lower window 320 having a larger size than the diameter of the plurality of lower pores 310 is formed in the front portion of the lower blocking part 300 according to the third embodiment of the present invention by cutting.

Although, in the illustrated embodiment, only one upper window 220 and only one lower window 320 are formed in the upper blocking part 200 and the lower blocking part 300, respectively, one or more upper windows 220 and one or more lower windows 320 may be formed.

Since the bone graft 10 according to the first embodiment of the present invention described above is inserted into the internal space 110 of the cage body 100 only through the rear insertion hole 400, it may be difficult for the bone graft 10 to be inserted sufficiently into the inner region of the internal space 110.

As shown in FIG. 16, the third embodiment of the present invention serves to address this problem, and the bone graft 10 may be inserted into the internal space 110 of the cage body 100 through the upper window 220, the lower window 320, and the rear insertion hole 400.

Since the bone graft 10 inserted through the upper window 220 and the lower window 320 may be directly inserted into the front parts of the upper and lower surfaces of the cage body 100, it may be easily inserted into the inner region of the internal space 110.

FIG. 17 is a perspective view showing the overall appearance of a box-shaped spinal cage structure according to a fourth embodiment of the present invention, FIG. 18 is a plan view showing the box-shaped spinal cage structure according to the fourth embodiment of the present invention, FIG. 19 is a bottom view showing the box-shaped spinal cage structure according to the fourth embodiment of the present invention, and FIG. 20 is a view showing a state of use of the box-shaped spinal cage structure according to the fourth embodiment of the present invention in which a bone graft is inserted into a cage body.

In the same manner as the first to third embodiments of the present invention, the box-shaped spinal cage structure according to the fourth embodiment of the present invention includes a cage body 100, an upper blocking part 200, a lower blocking part 300, and a rear insertion hole 400.

A plurality of upper pores 210 is perforated in the upper blocking part 200 in the upward and downward directions, a plurality of lower pores 310 is perforated in the lower blocking part 300 in the upward and downward directions, and a plurality of left and right structures 130 having a hollow interior is stacked on both side surfaces of the cage body 100.

Here, as shown in FIG. 18, at least one upper window 220 having a larger size than the diameter of the plurality of upper pores 210 is formed in the front portion of the upper blocking part 200 according to the third embodiment of the present invention by cutting.

However, as shown in FIG. 19, the fourth embodiment of the present invention differs from the third embodiment in that the lower blocking part 300 according to the fourth embodiment does not have a lower window 320, but includes only the plurality of lower pores 310.

Since the cage body 100 according to the third embodiment of the present invention described above has both the upper window 220 and the lower window 320, when the cage body 100 is inserted into the human body while the internal space 110 is filled with the bone graft 10, some of the bone graft 10 may be lost due to impact.

As shown in FIG. 20, the fourth embodiment of the present invention serves to address this problem, the bone graft 10 may be inserted into the internal space 110 of the cage body 100 through the upper window 220 and the rear insertion hole 400, and only the plurality of lower pores 310 may be formed in the lower blocking part 300.

FIG. 21 is a view showing an opened state of a front rotating part of a box-shaped spinal cage structure according to a fifth embodiment of the present invention, FIG. 22 is a view showing a closed state of the front rotating part according to the fifth embodiment of the present invention, FIG. 23 is an enlarged view of a coupling portion of the front rotating part according to the fifth embodiment of the present invention, and FIG. 24 is a view showing a state of use of the box-shaped spinal cage structure according to the fifth embodiment of the present invention in which a bone graft is inserted into a cage body.

In the same manner as the first to fourth embodiments of the present invention, the box-shaped spinal cage structure according to the fifth embodiment of the present invention includes a cage body 100, an upper blocking part 200, a lower blocking part 300, and a rear insertion hole 400.

In addition, the box-shaped spinal cage structure according to the fifth embodiment of the present invention further includes a front fastening part 151, a front fastening pin 152, and a front rotating part 150.

A plurality of upper pores 210 is perforated in the upper blocking part 200 in the upward and downward directions, a plurality of lower pores 310 is perforated in the lower blocking part 300 in the upward and downward directions, and a plurality of left and right structures 130 having a hollow interior is stacked on both side surfaces of the cage body 100. The front fastening part 151 is formed to protrude from the front surface of the cage body 100. Since the front surface of the cage body 100 is connected to the internal space 110, the bone graft 10 may be introduced into the internal space 110 through the front surface of the cage body 100.

The front fastening pin 152 is coupled to the front fastening part 151 in the upward and downward directions, and the front rotating part 150 is rotatably mounted on the front surface of the cage body 100 via the front fastening pin 152.

As shown in FIG. 21, the front rotating part 150 may be rotated to open the front surface of the cage body 100, and as shown in FIG. 22, the front rotating part 150 may be rotated to close the front surface of the cage body 100.

Since the bone graft 10 according to the first embodiment of the present invention described above is inserted into the internal space 110 of the cage body 100 only through the rear insertion hole 400, it may be difficult for the bone graft 10 to be inserted sufficiently into the inner region of the internal space 110.

As shown in FIG. 24, the fifth embodiment of the present invention serves to address this problem, and when the front rotating part 150 is opened, the bone graft 10 may be inserted into the internal space 110 of the cage body 100 through the front surface of the cage body 100 and the rear insertion hole 400.

Since the bone graft 10 inserted through a space opened by the front rotating part 150 may be directly inserted into the front part of the cage body 100, it may be easily inserted into the inner region of the internal space 110.

FIG. 25 is a view showing an opened state of a front sliding part of a box-shaped spinal cage structure according to a sixth embodiment of the present invention, FIG. 26 is a view showing a closed state of the sliding part according to the sixth embodiment of the present invention, FIG. 27 is a cross-sectional view taken along line B-B' of FIG. 26 according to the sixth embodiment of the present invention, and FIG. 28 is a view showing a state of use of the box-shaped spinal cage structure according to the sixth embodiment of the present invention in which a bone graft is inserted into a cage body.

In the same manner as the first to fifth embodiments of the present invention, the box-shaped spinal cage structure according to the sixth embodiment of the present invention includes a cage body 100, an upper blocking part 200, a lower blocking part 300, and a rear insertion hole 400.

In addition, the box-shaped spinal cage structure according to the sixth embodiment of the present invention further includes a pair of front rails 163 and a front sliding part 160.

A plurality of upper pores 210 is perforated in the upper blocking part 200 in the upward and downward directions, a plurality of lower pores 310 is perforated in the lower blocking part 300 in the upward and downward directions, and a plurality of left and right structures 130 having a hollow interior is stacked on both side surfaces of the cage body 100.

The pair of front rails 163 is coupled to the front surface of the cage body 100 in the leftward and rightward directions. Since the front surface of the cage body 100 is connected to the internal space 110, the bone graft 10 may be introduced into the internal space 110 through the front surface of the cage body 100.

The front sliding part 160 is slidably fastened to the pair of front fails 163. A pair of sliding grooves 161 is formed on the rear surface of the front sliding part 160, and the pair of sliding grooves 161 is formed in a shape corresponding to the pair of front rails 163 so that the pair of front rails 163 is inserted into the pair of sliding grooves 161.

As shown in FIG. 25, the front sliding part 160 may move to the right to open the front surface of the cage body 100, and as shown in FIG. 26, the front sliding part 160 may move to the left to close the front surface of the cage body 100.

Further, a front protrusion 164 is formed to protrude from the front surface of the cage body 100, and a sliding engagement part 162 is formed to be recessed in the left side surface of the front sliding part 160. The sliding engagement part 162 is disposed to face the front protrusion 164, and is engaged with the front protrusion 164.

That is, when the front sliding part 160 is closed, as shown in FIG. 26, the sliding engagement part 162 and the front protrusion 164 are completely engaged with each other so that the front sliding part 160 may be coupled to the cage body 100 as if the front sliding part 160 was formed almost integrally with the cage boy 100.

Since the bone graft 10 according to the first embodiment of the present invention described above is inserted into the internal space 110 of the cage body 100 only through the rear insertion hole 400, it may be difficult for the bone graft 10 to be inserted sufficiently into the inner region of the internal space 110.

As shown in FIG. 28, the sixth embodiment of the present invention serves to address this problem, and when the front sliding part 160 is opened, the bone graft 10 may be inserted into the internal space 110 of the cage body 100 through the front surface of the cage body 100 and the rear insertion hole 400.

Since the bone graft 10 inserted through a space opened by the front sliding part 160 may be directly inserted into the front part of the cage body 100, it may be easily inserted into the inner region of the internal space 110.

FIG. 29 is a view showing an opened state of a front locking part of a box-shaped spinal cage structure according to a seventh embodiment of the present invention, FIG. 30 is a view showing a closed state of the front locking part according to the seventh embodiment of the present invention, FIG. 31 is a cross-sectional view taken along line C-C' of FIG. 30 according to the seventh embodiment of the present invention, and FIG. 32 is a view showing a state of use of the box-shaped spinal cage structure according to the seventh embodiment of the present invention in which a bone graft is inserted into a cage body.

In the same manner as the first to sixth embodiments of the present invention, the box-shaped spinal cage structure according to the seventh embodiment of the present invention includes a cage body 100, an upper blocking part 200, a lower blocking part 300, and a rear insertion hole 400.

In addition, the box-shaped spinal cage structure according to the seventh embodiment of the present invention further includes a pair of front engagement parts 173 and a front locking part 170.

A plurality of upper pores 210 is perforated in the upper blocking part 200 in the upward and downward directions, a plurality of lower pores 310 is perforated in the lower blocking part 300 in the upward and downward directions, and a plurality of left and right structures 130 having a hollow interior is stacked on both side surfaces of the cage body 100.

The pair of front engagement parts 173 is formed to protrude inwardly from both inner sides of the front surface of the cage body 100. Since the front surface of the cage body 100 is connected to the internal space 110, the bone graft 10 may be introduced into the internal space 110 through the front surface of the cage body 100.

The front locking part 170 is engaged with and fastened to the pair of front engagement parts 173. A pair of hooks 171 is formed to protrude rearwardly from the rear surface of the front locking part 170, and the pair of hooks 171 is hooked to the pair of front engagement parts 173. The pair of hooks 171 may be formed of a material having elastic restoring force to be deformable in the leftward and rightward directions.

As shown in FIG. 29, the hooks 171 of the front locking part 170 may be released from the front engagement parts 173 to open the front surface of the cage body 100, and as shown in FIG. 30, the hooks 171 of the front locking part 170 may be fastened to the front engagement parts 183 to close the front surface of the cage body 100.

Further, engagement slopes 174 formed as inclined surfaces having a predetermined angle are formed on the front surfaces of the front engagement parts 173, and hook slopes 172 formed as inclined surfaces having a predetermined angle are formed on the rear surfaces of the hooks 171. The pair of hooks 171 may be deformed in the leftward and rightward directions by the engagement slopes 174 and hook slopes 172.

Since the bone graft 10 according to the first embodiment of the present invention described above is inserted into the internal space 110 of the cage body 100 only through the rear insertion hole 400, it may be difficult for the bone graft 10 to be inserted sufficiently into the inner region of the internal space 110.

As shown in FIG. 32, the seventh embodiment of the present invention serves to address this problem, and when the front locking part 170 is opened, the bone graft 10 may be inserted into the internal space 110 of the cage body 100 through the front surface of the cage body 100 and the rear insertion hole 400.

Since the bone graft 10 inserted through a space opened by the front locking part 170 may be directly inserted into the front part of the cage body 100, it may be easily inserted into the inner region of the internal space 110.

FIG. 33 is a view showing a separated state of a set screw of a box-shaped spinal cage structure according to an eighth embodiment of the present invention, and FIG. 34 is a view showing a fastened state of the set screw according to the eighth embodiment of the present invention.

In the same manner as the first to seventh embodiments of the present invention, the box-shaped spinal cage structure according to the eighth embodiment of the present invention includes a cage body 100, an upper blocking part 200, a lower blocking part 300, and a rear insertion hole 400.

In addition, the box-shaped spinal cage structure according to the eighth embodiment of the present invention further includes a set screw 420.

A plurality of upper pores 210 is perforated in the upper blocking part 200 in the upward and downward directions, a plurality of lower pores 310 is perforated in the lower blocking part 300 in the upward and downward directions, and a plurality of left and right structures 130 having a hollow interior is stacked on both side surfaces of the cage body 100.

The set screw 420 is inserted and fastened into the rear insertion hole 400 of the cage body 100 to block the internal space 110 of the cage body 100 from the outside. Here, a screw hole 421 is formed through the center of the set screw 420, and the diameter of the screw hole 421 may be smaller than the diameter of the rear insertion hole 400.

As in the above-described first embodiment of the present invention, the bone graft 10 inserted into the internal space 110 of the cage body 100 through the rear insertion hole 400 may be gradually lost before being completely ossified as a patient goes about his or her daily life.

The eighth embodiment of the present invention serves to address this problem, and the set screw 420 is inserted and fastened into the rear insertion hole 400 to block the internal space 110 from the outside, thereby being capable of preventing loss of the bone graft 10 as much as possible.

FIG. 35 is a view showing an opened state of a rear rotating part of a box-shaped spinal cage structure according to a ninth embodiment of the present invention, and FIG. 36 is a view showing a closed state of the rear rotating part according to the ninth embodiment of the present invention.

In the same manner as the first to eighth embodiments of the present invention, the box-shaped spinal cage structure according to the ninth embodiment of the present invention includes a cage body 100, an upper blocking part 200, a lower blocking part 300, and a rear insertion hole 400.

In addition, the box-shaped spinal cage structure according to the ninth embodiment of the present invention further includes a rear fastening pin 431 and a rear rotating part 430.

A plurality of upper pores 210 is perforated in the upper blocking part 200 in the upward and downward directions, a plurality of lower pores 310 is perforated in the lower blocking part 300 in the upward and downward directions, and a plurality of left and right structures 130 having a hollow interior is stacked on both side surfaces of the cage body 100.

The rear fastening pin 431 is coupled to the rear surface of the cage body 100 in the upward and downward directions. The rear rotating part 430 is mounted rotatably on the rear surface of the cage body 100 via the rear fastening pin 431.

The rear rotating part 430 has a size sufficient to sufficiently close the rear insertion hole 400 of the cage body 100, and closes the rear insertion hole 400 to block the internal space 110 of the cage body 100 from the outside.

As in the above-described first embodiment of the present invention, the bone graft 10 inserted into the internal space 110 of the cage body 100 through the rear insertion hole 400 may be gradually lost before being completely ossified as a patient goes about his or her daily life.

The ninth embodiment of the present invention serves to address this problem, and the rear rotating part 430 closes the rear insertion hole 400 to block the internal space 110 from the outside, thereby being capable of preventing loss of the bone graft 10 as much as possible.

FIG. 37 is a view showing a closed of a rear movable part of a box-shaped spinal cage structure according to a tenth embodiment of the present invention, and FIG. 38 is a cross-sectional view taken along line D-D' of FIG. 37 according to the tenth embodiment of the present invention.

In the same manner as the first to ninth embodiments of the present invention, the box-shaped spinal cage structure according to the tenth embodiment of the present invention includes a cage body 100, an upper blocking part 200, a lower blocking part 300, and a rear insertion hole 400.

In addition, the box-shaped spinal cage structure according to the tenth embodiment of the present invention further includes a rear lateral hole 441 and a rear movable part 440.

A plurality of upper pores 210 is perforated in the upper blocking part 200 in the upward and downward directions, a plurality of lower pores 310 is perforated in the lower blocking part 300 in the upward and downward directions, and a plurality of left and right structures 130 having a hollow interior is stacked on both side surfaces of the cage body 100.

The rear lateral hole 441 is perforated in the lateral direction, i.e., in the leftward and rightward directions, in the rear surface of the cage body 100, and the rear movable part 440 is accommodated in the rear lateral hole 441 and may move left and right within the rear lateral hole 441.

The rear lateral hole 441 and the rear movable part 440 are formed to have greater sizes than the size of the rear insertion hole 400 of the cage body 100, and the rear movable part 440 closes the rear insertion hole 440 to block the internal space 110 of the cage body 100 from the outside.

As in the above-described first embodiment of the present invention, the bone graft 10 inserted into the internal space 110 of the cage body 100 through the rear insertion hole 400 may be gradually lost before being completely ossified as a patient goes about his or her daily life.

The tenth embodiment of the present invention serves to address this problem, and the rear movable part 440 closes the rear insertion hole 440 to block the internal space 110 of the cage body 100 from the outside, thereby being capable of preventing loss of the bone graft 10 as much as possible.

As is apparent from the above description, a box-shaped spinal cage structure having the above configuration according to the present invention has an upper blocking part coupled to the upper surface of a cage body and a lower blocking part coupled to the lower surface of the cage body, thereby being capable of significantly reducing the amount of bone graft loss even if an impact occurs when the cage body is inserted into the human body.

In addition, the box-shaped spinal cage structure according to the present invention has a plurality of upper pores perforated in the upper blocking part, a plurality of lower pores perforated in the lower blocking part, and left and right structures stacked on both side surfaces of the cage body, thereby enabling stable bone fusion due to contact of a bone graft in the cage body with the outside.

The present invention described above is not limited to the above-described embodiment and the accompanying drawings, and those skilled in the art will appreciate that various modifications, additions and substitutions are possible, without departing from the scope and spirit of the invention as disclosed in the accompanying claims.

The invention claimed is:

1. A box-shaped spinal cage structure comprising:
a cage body having an internal space formed therein;
an upper blocking part coupled to an upper surface of the cage body to block the internal space of the cage body from outside;
a lower blocking part coupled to a lower surface of the cage body to block the internal space of the cage body from the outside;
a rear insertion hole formed through a rear surface of the cage body such that a bone graft is insertable into the internal space of the cage body through the rear insertion hole;
a pair of front engagement parts protruding inwardly from both inner sides of a front surface of the cage body; and
a front locking part having a pair of hooks, the pair of hooks protruding rearwardly from a rear surface of the front locking part to be hooked and fastened to the pair of front engagement parts,
wherein the upper blocking part includes a plurality of upper pores and the lower blocking part includes a plurality of lower pores, thereby providing the upper blocking part and the lower blocking part with porosity,
wherein the pair of hooks include a material having elastic restoring force, allowing the pair of hooks to be deformed in leftward and rightward directions,
wherein the front locking part is configured to open or close the front surface of the cage body,
wherein, when the front locking part is coupled to the cage body through the front surface of the cage body, the front locking part is spaced apart from the rear insertion hole such that the cage body is disposed between the front locking part and the rear insertion hole,
wherein, when the front locking part is coupled to the cage body through the front surface of the cage body, the front surface of the cage body is completely sealed,
wherein, when the front locking part is separated from the front surface of the cage body, the front surface of the cage body communicates with the internal space of the cage body,
wherein the rear surface of the cage body is configured to be in communication with the internal space of the cage body through the rear insertion hole, and
wherein, when the front locking part is opened, the bone graft is configured to be inserted into the internal space of the cage body selectively through the front surface or the rear insertion hole.

2. The box-shaped spinal cage structure according to claim 1, wherein a plurality of left and right structures having a hollow interior is stacked on both side surfaces of the cage body.

3. The box-shaped spinal cage structure according to claim 1, wherein:
a first plurality of left and right structures is stacked on one side surface of the cage body, each of the first plurality of left and right structures includes a first hollow interior, and a side window having a larger size than a size of the first hollow interior is disposed in the one side surface of the cage body such that the bone graft is insertable into the internal space of the cage body through the side window; and
a second plurality of left and right structures is stacked on a remaining side surface of the cage body, and each of the second plurality of left and right structures includes a second hollow interior.

4. The box-shaped spinal cage structure according to claim 1, further comprising:
at least one upper window disposed on one side of the upper blocking part and having a larger size than a size of each of the plurality of upper pores; and
at least one lower window disposed on one side of the lower blocking part and having a larger size than a size of each of the plurality of lower pores,
wherein the bone graft is insertable into the internal space of the cage body through the at least one upper window and the at least one lower window.

5. The box-shaped spinal cage structure according to claim 1, further comprising at least one upper window disposed on one side of the upper blocking part and having a larger size than a size of each of the plurality of upper pores, wherein:
the bone graft is insertable into the internal space of the cage body through the at least one upper window; and
the plurality of lower pores is formed in the lower blocking part.

6. The box-shaped spinal cage structure according to claim 1, further comprising:
engagement slopes disposed on front surfaces of the front engagement parts, and including first inclined surfaces each having a first predetermined angle; and
hook slopes disposed on rear surfaces of the hooks, and including second inclined surfaces each having a second predetermined angle.

7. The box-shaped spinal cage structure according to claim 1, further comprising a set screw inserted and fastened into the rear insertion hole to block the internal space of the cage body from the outside.

8. The box-shaped spinal cage structure according to claim 7, wherein a screw hole is formed through a center of the set screw, and a diameter of the screw hole is smaller than a diameter of the rear insertion hole.

9. The box-shaped spinal cage structure according to claim 1, further comprising:
a rear fastening pin coupled to the rear surface of the cage body in upward and downward directions; and
a rear rotating part mounted rotatably on the rear surface of the cage body via the rear fastening pin,
wherein the rear rotating part is configured to open or close the rear insertion hole, and when the rear rotating part is closed, the bone graft is not discharged outside the cage body through the rear insertion hole.

10. The box-shaped spinal cage structure according to claim 1, further comprising:
a rear lateral hole perforated in leftward and rightward directions in the rear surface of the cage body; and
a rear movable part disposed in the rear lateral hole to move left and right within the rear lateral hole,
wherein the rear movable part is configured to open or close the rear insertion hole, and when the rear movable part is closed, the bone graft is not discharged outside the cage body through the rear insertion hole.

11. The box-shaped spinal cage structure according to claim 1, further comprising:

a device fixing unit inserted into the rear insertion hole and configured to accommodate the bone graft therein; and an impactor configured to enter an inside of the device fixing unit to insert the bone graft accommodated in the device fixing unit into the internal space of the cage body.

* * * * *